United States Patent
Field et al.

(10) Patent No.: US 7,666,194 B2
(45) Date of Patent: *Feb. 23, 2010

(54) SURGICAL SUTURING INSTRUMENT AND METHOD OF USE

(75) Inventors: Frederic P. Field, North Hampton, NH (US); Douglas A. Fogg, Merrimac, MA (US); Gregory E. Sancoff, North Hampton, NH (US)

(73) Assignee: Onux Medical, Inc., Hampton, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/352,600

(22) Filed: Jan. 28, 2003

(65) Prior Publication Data

US 2003/0114863 A1    Jun. 19, 2003

Related U.S. Application Data

(63) Continuation of application No. 10/082,510, filed on Oct. 19, 2001, now Pat. No. 6,511,489, which is a continuation-in-part of application No. 09/818,300, filed on Mar. 27, 2001, now Pat. No. 6,527,785.

(51) Int. Cl.
    *A61B 17/04*    (2006.01)
(52) U.S. Cl. .................................... 606/144
(58) Field of Classification Search ............... 606/103, 606/144, 148, 228, 139, 151, 157
    See application file for complete search history.

(56) References Cited

U.S. PATENT DOCUMENTS 919,138 A    4/1909    Drake et al.

(Continued)

FOREIGN PATENT DOCUMENTS

DE    2927143 A1 *    10/1978

(Continued)

OTHER PUBLICATIONS

Auto Suture Company, VCS Clip Applier System, undated.

*Primary Examiner*—Michael J Milano
*Assistant Examiner*—Victor X Nguyen
(74) *Attorney, Agent, or Firm*—Wolf, Greenfield & Sacks, P.C.

(57) ABSTRACT

A device is disclosed for introducing a flexible elongated element through at least two portions of a subject. In a preferred embodiment, the device includes a proximal end and a distal end, and an advancement unit for longitudinally advancing the flexible elongated element toward the distal end of the device such that a proximal end of the elongated element may exit from the distal end of the device with sufficient force to pass through the subject. The device also includes a curved die at the distal end of the device for imparting a looping configuration to portions of the flexible elongated element exiting the distal end of the device, and a curved guide at the distal end for receiving the looped flexible elongated element as it returns to the distal end of the device. In a further feature of the invention, a cutting mechanism is provided to permit the looped flexible elongated element to be separated from the remainder of the flexible elongated element. And in a further feature of the invention, the cutting mechanism is adapted to deform the trailing end of the looped flexible elongated element so that the trailing end is forced distally, toward the subject being sutured.

26 Claims, 35 Drawing Sheets

U.S. PATENT DOCUMENTS

| | | | |
|---|---|---|---|
| 1,449,087 A | 3/1923 | Bugbee | |
| 2,579,192 A | 12/1951 | Kohl | |
| 2,613,562 A | 10/1952 | Clark | |
| 2,897,820 A | 8/1959 | Tauber | |
| 3,013,559 A | 12/1961 | Thomas | |
| 3,404,677 A | 10/1968 | Springer | |
| 3,470,875 A | 10/1969 | Johnson | |
| 3,545,444 A | 12/1970 | Green | |
| 3,584,628 A | 6/1971 | Green | |
| 3,675,688 A | 7/1972 | Bryan | |
| 3,735,762 A | 5/1973 | Bryan | |
| 3,802,438 A | 4/1974 | Wolvek | |
| 3,807,407 A | 4/1974 | Schweizer | |
| 3,840,017 A | 10/1974 | Violante et al. | |
| 3,841,521 A | 10/1974 | Jarvik | |
| 3,858,783 A | 1/1975 | Kapitanov et al. | |
| 3,877,570 A | 4/1975 | Barry | |
| 3,959,960 A | 6/1976 | Santos | |
| RE28,932 E | 8/1976 | Noiles | |
| 4,006,747 A | 2/1977 | Kronenthal et al. | |
| 4,027,608 A | 6/1977 | Arbuckle | |
| 4,103,690 A | 8/1978 | Harris | |
| 4,109,658 A | 8/1978 | Hughes | |
| 4,204,541 A | 5/1980 | Kapitanov | |
| 4,235,177 A | 11/1980 | Arbuckle | |
| 4,235,238 A | 11/1980 | Ogiu et al. | |
| 4,258,716 A | 3/1981 | Sutherland | |
| 4,306,560 A * | 12/1981 | Harris | 606/129 |
| 4,453,661 A | 6/1984 | Genyk et al. | |
| 4,462,404 A | 7/1984 | Schwarz et al. | |
| 4,474,181 A | 10/1984 | Schenck | |
| 4,553,543 A | 11/1985 | Amarasinghe | |
| 4,557,265 A | 12/1985 | Andersson | |
| 4,583,541 A | 4/1986 | Barry | |
| 4,595,007 A | 6/1986 | Mericle et al. | |
| 4,602,636 A | 7/1986 | Noiles | |
| 4,607,637 A | 8/1986 | Berggren et al. | |
| 4,610,383 A | 9/1986 | Rothfuss et al. | |
| 4,612,933 A | 9/1986 | Brinkerhoff | |
| 4,624,257 A | 11/1986 | Berggren et al. | |
| 4,643,190 A | 2/1987 | Heimberger | |
| 4,644,651 A | 2/1987 | Jacobsen | |
| 4,669,473 A | 6/1987 | Richards et al. | |
| 4,705,040 A | 11/1987 | Mueller et al. | |
| 4,741,330 A | 5/1988 | Hayhurst | |
| 4,747,358 A | 5/1988 | Moll et al. | |
| 4,760,848 A | 8/1988 | Hasson | |
| 4,763,669 A | 8/1988 | Jaeger | |
| 4,803,984 A | 2/1989 | Narayanan et al. | |
| 4,819,635 A | 4/1989 | Shapiro | |
| 4,890,615 A | 1/1990 | Caspari et al. | |
| 4,901,721 A | 2/1990 | Hakki | |
| 4,915,107 A | 4/1990 | Rebuffat et al. | |
| 4,923,461 A | 5/1990 | Caspari et al. | |
| 4,935,027 A | 6/1990 | Yoon | |
| 4,938,214 A | 7/1990 | Specht et al. | |
| 4,941,466 A | 7/1990 | Romano | |
| 4,955,887 A | 9/1990 | Zirm | |
| 4,957,498 A | 9/1990 | Caspari et al. | |
| 4,966,600 A | 10/1990 | Songer et al. | |
| 5,002,564 A | 3/1991 | McGregor et al. | |
| 5,004,469 A | 4/1991 | Palmieri et al. | |
| 5,021,059 A | 6/1991 | Kensey | |
| 5,037,433 A | 8/1991 | Wilk et al. | |
| 5,133,735 A | 7/1992 | Slater et al. | |
| 5,147,373 A | 9/1992 | Ferzli | |
| 5,161,725 A | 11/1992 | Murray | |
| 5,171,256 A | 12/1992 | Smith et al. | |
| 5,174,300 A | 12/1992 | Bales et al. | |
| 5,192,298 A | 3/1993 | Smith et al. | |
| 5,211,650 A | 5/1993 | Noda et al. | |
| 5,217,465 A | 6/1993 | Steppe | |
| 5,219,357 A | 6/1993 | Honkanen et al. | |
| 5,234,453 A | 8/1993 | Smith et al. | |
| 5,242,459 A | 9/1993 | Buelna | |
| 5,254,126 A | 10/1993 | Filipi et al. | |
| 5,261,917 A | 11/1993 | Hasson et al. | |
| 5,290,284 A | 3/1994 | Adair | |
| 5,304,183 A | 4/1994 | Gourlay et al. | |
| 5,306,281 A | 4/1994 | Beurrier | |
| 5,308,353 A | 5/1994 | Beurrier | |
| 5,308,357 A | 5/1994 | Lichtman | |
| 5,324,308 A | 6/1994 | Pierce | |
| 5,333,625 A | 8/1994 | Klein | |
| 5,334,199 A | 8/1994 | Yoon | |
| 5,356,424 A | 10/1994 | Buzerak et al. | |
| 5,370,658 A | 12/1994 | Scheller et al. | |
| 5,372,604 A | 12/1994 | Trott | |
| 5,386,741 A | 2/1995 | Rennex | |
| 5,387,221 A | 2/1995 | Bisgaard et al. | |
| 5,411,522 A | 5/1995 | Trott | |
| 5,417,700 A * | 5/1995 | Egan | 606/144 |
| 5,417,701 A | 5/1995 | Holmes | |
| 5,423,821 A | 6/1995 | Pasque | |
| 5,431,670 A | 7/1995 | Holmes | |
| 5,437,681 A * | 8/1995 | Meade et al. | 606/145 |
| 5,439,446 A | 8/1995 | Barry | |
| 5,447,512 A | 9/1995 | Wilson | |
| 5,458,609 A | 10/1995 | Gordon et al. | |
| 5,474,554 A | 12/1995 | Ku | |
| 5,478,093 A | 12/1995 | Eibl et al. | |
| 5,496,334 A | 3/1996 | Klundt et al. | |
| 5,498,256 A | 3/1996 | Furnish | |
| 5,499,990 A * | 3/1996 | Schulken et al. | 606/144 |
| 5,500,001 A | 3/1996 | Trott | |
| 5,501,683 A * | 3/1996 | Trott | 606/72 |
| 5,501,688 A | 3/1996 | Whiteside et al. | |
| 5,501,692 A | 3/1996 | Riza | |
| 5,501,698 A | 3/1996 | Roth et al. | |
| 5,522,820 A | 6/1996 | Caspari et al. | |
| 5,527,321 A | 6/1996 | Hinchliffe | |
| 5,527,322 A | 6/1996 | Klein | |
| 5,571,119 A | 11/1996 | Atala | |
| 5,578,044 A | 11/1996 | Gordon | |
| 5,582,616 A | 12/1996 | Bolduc | |
| 5,618,306 A | 4/1997 | Roth et al. | |
| 5,665,096 A | 9/1997 | Yoon et al. | |
| 5,674,230 A | 10/1997 | Tovey et al. | |
| 5,690,653 A | 11/1997 | Richardson et al. | |
| 5,709,693 A | 1/1998 | Taylor | |
| 5,713,910 A | 2/1998 | Gordon | |
| 5,720,766 A | 2/1998 | Zang et al. | |
| 5,728,112 A | 3/1998 | Yoon | |
| 5,755,728 A | 5/1998 | Maki et al. | |
| 5,759,188 A | 6/1998 | Yoon | |
| 5,766,186 A * | 6/1998 | Faraz et al. | 606/145 |
| 5,766,217 A | 6/1998 | Christy | |
| 5,776,150 A | 7/1998 | Nolan et al. | |
| 5,782,844 A | 7/1998 | Yoon | |
| 5,792,152 A | 8/1998 | Klein | |
| 5,797,927 A | 8/1998 | Yoon | |
| 5,799,672 A | 9/1998 | Hansbury | |
| 5,810,851 A * | 9/1998 | Yoon | 606/148 |
| 5,810,882 A | 9/1998 | Bolduc | |
| 5,814,054 A | 9/1998 | Kortenbach et al. | |
| 5,824,008 A | 10/1998 | Bolduc et al. | |
| 5,830,221 A | 11/1998 | Stein | |
| 5,830,234 A | 11/1998 | Wojciechowicz et al. | |
| 5,891,140 A * | 4/1999 | Ginn et al. | 606/48 |
| 5,911,727 A | 6/1999 | Taylor | |
| 5,972,004 A | 10/1999 | Williamson, IV | |
| 6,048,351 A | 4/2000 | Gordon et al. | |
| 6,074,404 A | 6/2000 | Stalker | |
| 6,090,063 A * | 7/2000 | Makower et al. | 604/13 |

| | | | | | | |
|---|---|---|---|---|---|---|
| 6,099,537 A | 8/2000 | Sugai | | 2003/0105475 A1 | 6/2003 | Sancoff et al. |
| 6,187,019 B1 | 2/2001 | Stefanchik | | 2003/0105476 A1 | 6/2003 | Sancoff et al. |
| 6,206,893 B1 | 3/2001 | Klein | | 2003/0135226 A1 | 7/2003 | Bolduc |
| 6,296,656 B1 | 10/2001 | Bolduc | | 2003/0171761 A1 | 9/2003 | Sancoff et al. |
| 6,331,182 B1 | 12/2001 | Tiefenbrun et al. | | 2004/0073237 A1 | 4/2004 | Leinsing et al. |
| 6,332,889 B1 | 12/2001 | Sancoff et al. | | 2004/0087979 A1 | 5/2004 | Field et al. |
| 6,383,208 B1 | 5/2002 | Sancoff et al. | | 2004/0092967 A1 | 5/2004 | Sancoff et al. |
| 6,454,778 B2 | 9/2002 | Kortenbach | | 2004/0133221 A1 | 7/2004 | Sancoff et al. |
| 6,511,489 B2 | 1/2003 | Field et al. | | 2004/0158267 A1 | 8/2004 | Sancoff et al. |
| 6,514,263 B1 | 2/2003 | Stefanchik | | 2004/0254592 A1 | 12/2004 | DiCarlo et al. |
| 6,517,553 B2 | 2/2003 | Klein | | 2005/0038449 A1 | 2/2005 | Sancoff et al. |
| 6,520,973 B1 | 2/2003 | McGarry et al. | | 2005/0043747 A1 | 2/2005 | Field et al. |
| 6,527,785 B2 | 3/2003 | Sancoff et al. | | 2005/0070922 A1 | 3/2005 | Field et al. |
| 6,530,932 B1 | 3/2003 | Swayze | | | | |
| 6,562,051 B1 | 5/2003 | Bolduc | | FOREIGN PATENT DOCUMENTS | | |
| 6,663,641 B1 * | 12/2003 | Kovac et al. ............... 606/144 | | DE | 2927143 | 1/1980 |
| 6,663,643 B2 | 12/2003 | Field et al. | | EP | 0121362 | 10/1984 |
| 6,679,895 B1 | 1/2004 | Sancoff et al. | | GB | 2025236 | 1/1980 |
| 6,682,540 B1 | 1/2004 | Sancoff et al. | | JP | 5237123 | 9/1993 |
| 6,740,099 B1 | 5/2004 | Doyle et al. | | US | 0121362 | * 10/1984 |
| 6,767,352 B2 | 7/2004 | Field et al. | | WO | WO 96/27331 | 9/1996 |
| 6,786,913 B1 | 9/2004 | Sancoff et al. | | WO | WO9719643 | 6/1997 |
| 2002/0128666 A1 | 9/2002 | Sancoff et al. | | WO | WO9912482 | 3/1999 |
| 2003/0023250 A1 | 1/2003 | Watschke et al. | | WO | WO 02/34167 | 5/2002 |
| 2003/0028202 A1 | 2/2003 | Sancoff et al. | | WO | WO 02/43569 | 6/2002 |
| 2003/0083695 A1 | 5/2003 | Morris et al. | | | | |
| 2003/0105473 A1 | 6/2003 | Miller | | * cited by examiner | | |

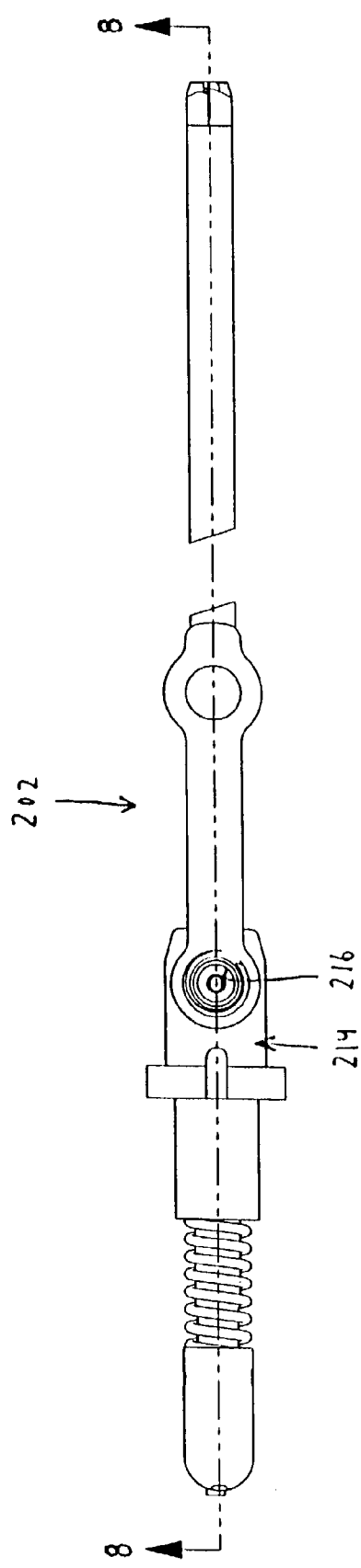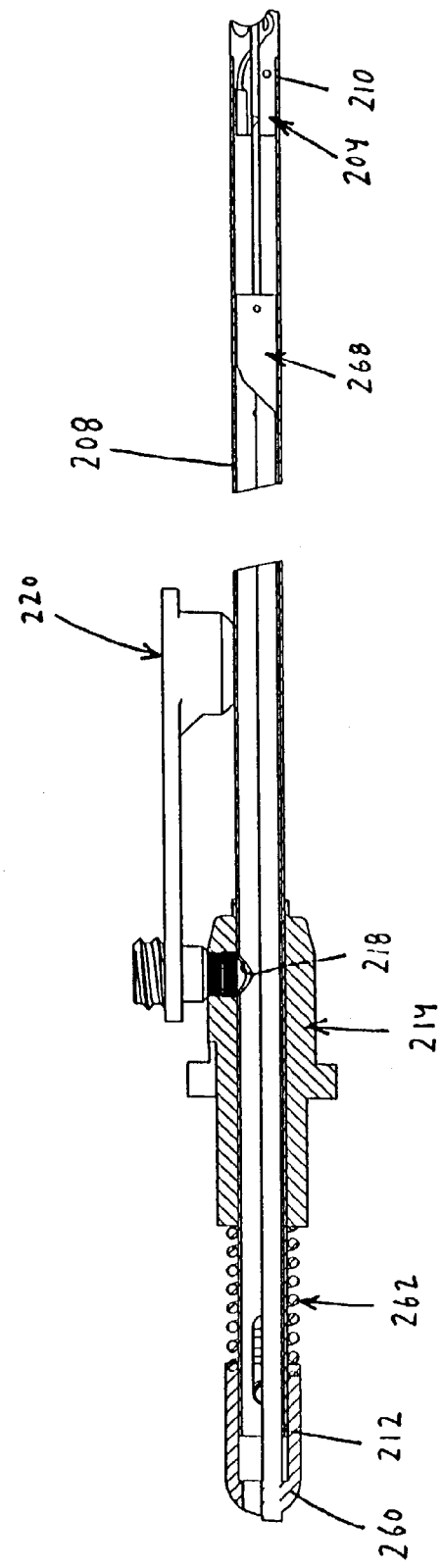
FIG. 7
FIG. 8

SURGICAL SUTURING INSTRUMENT AND METHOD OF USE

REFERENCE TO PENDING PRIOR PATENT APPLICATION

This is a continuation of prior U.S. patent application Ser. No. 10/082,510, filed Oct. 19, 2001 now U.S. Pat. No. 6,511,489 by Frederic P. Field et al. for SURGICAL SUTURING INSTRUMENT AND METHOD OF USE, which patent application is a continuation-in-part of prior U.S. patent application Ser. No. 09/818,300, filed Mar. 27, 2001 now U.S. Pat. No. 6,527,785 by Gregory E. Sancoff et al. for SURGICAL SUTURING INSTRUMENT AND METHOD OF USE, which patent application in turn claims benefit of (1) prior U.S. patent application Ser. No.

09/368,273, filed Aug. 3, 1999 by Gregory E. Sancoff et al. for SURGICAL SUTURING INSTRUMENT AND METHOD OF USE, and (2) prior U.S. Provisional Patent Application Ser. No. 60/192,487, filed Mar. 27, 2000 by Gregory E. Sancoff et al. for SURGICAL SUTURING INSTRUMENT AND METHOD OF USE.

This patent application also claims benefit of pending prior U.S. Provisional Patent application Ser. No. 60/242,269, filed Oct. 20, 2000 by Frederic P. Field et al. for SURGICAL SUTURING INSTRUMENT AND METHOD OF USE.

This patent application also claims benefit of pending prior U.S. Provisional Patent Application Ser. No. 60/241,936, filed Oct. 20, 2000 by Bruce B. Adams et al. for SURGICAL SUTURING INSTRUMENT AND METHOD OF USE.

The five above-identified patent applications are hereby incorporated herein by reference.

FIELD OF THE INVENTION

This invention relates to medical instruments and procedures in general, and more particularly to suturing instruments and methods for suturing.

BACKGROUND OF THE INVENTION

Suturing instruments are typically used to secure together two or more portions of a subject patient (e.g., tissue such as muscle or skin) or to attach an object to the patient (e.g., to attach a piece of surgical mesh to the abdominal wall of the patient during hernia repair surgery).

Certain suturing instruments employ a needle that precedes a length of suture material through a subject.

For example, U.S. Pat. Nos. 3,470,875; 4,027,608; 4,747,358; 5,308,353; 5,674,230; 5,690,653; 5,759,188; and 5,766,186 generally disclose suturing instruments in which a needle, with trailing suture material, is passed through a subject.

U.S. Pat. Nos. 4,890,615; 4,935,027; 5,417,700; and 5,728,112 generally disclose suturing instruments in which suture material is passed through the end of a hollow needle after that needle has been passed through a subject.

With all of the foregoing devices, a needle must be passed through the subject in order to deploy the suture. This has the disadvantage that the needle typically leaves a larger hole in the subject than is necessary to accommodate only the suture material itself. In this respect it should be appreciated that it is generally desirable to alter each portion of the material being sutured (e.g., tissue) as little as possible during the suturing process.

A suturing instrument has been devised which permits the suture material itself to pierce the subject without the use of a needle. However, this device does not permit adequate flexibility with regard to the type of fastening which may be effected.

More particularly, U.S. Pat. No. 5,499,990 discloses a suturing instrument having a pair of jaws at its distal end for clamping together two portions of a subject. A 0.25 mm stainless steel suturing wire is advanced to the distal end of the suturing instrument, whereupon the distal end of the suturing wire is caused to travel in a spiral direction so as to create stitches joining together the two portions of the subject. After the spiral is formed, the beginning and end portions of the suture may be bent toward the tissue in order to inhibit retraction of the suture wire into the tissue upon removal of the suturing instrument. The stainless steel wire is sufficiently firm to hold this locking set. In addition, after the spiral is formed, the radius of the deployed suture spiral may then be decreased by advancing an outer tube over a portion of the distal end of the instrument. Again, the stainless steel wire is sufficiently firm to hold this reducing set.

Unfortunately, however, such a system does not permit adequate flexibility with regard to the type of fastening which may be effected. More particularly, the suturing instrument of U.S. Pat. No. 5,499,990 must clamp the two portions of the subject between its two jaws in order to effect suturing. Such a construction can be inadequate where it is difficult or even impossible to clamp the two portions of the subject between the instrument's jaws, e.g., where the two portions of the subject are too thick to be spanned by the jaws, or where the angle of approach prevents the jaws from clamping together the two portions of the subject, etc.

U.S. Pat. No. 4,453,661 discloses a surgical instrument having a pair of jaws at its distal end for clamping together two portions of a subject and applying staples thereto. The staples are formed from the distal end of a length of wire. More particularly, the distal end of the wire is passed through a subject and thereafter contacts a die that causes the wire to bend, thereby forming the staple. The wire is sufficiently firm to take on the set imposed by the die. The staple portion is then cut away from the remainder of the wire by a knife.

Again, such a system suffers from the fact that it does not permit adequate flexibility with regard to the type of fastening which may be effected, since the surgical instrument must clamp the two portions of the subject between its two jaws in order to effect stapling, and this can be difficult or even impossible to achieve in certain circumstances, e.g., where the two portions of the subject are too thick to be spanned by the jaws, or where the angle of approach prevents clamping, etc.

There is a need, therefore, for a new suturing device that permits minimally disruptive suturing and provides increased flexibility in the application of the suture material.

SUMMARY OF THE INVENTION

The present invention comprises a novel device and method for deploying a flexible elongated element through a subject so as to effect suturing.

In one embodiment of the invention, the device includes a proximal end and a distal end, and an advancement unit for longitudinally advancing the flexible elongated element toward the distal end of the device such that a distal end of the flexible elongated element may exit from the distal end of the device with sufficient force to pass through the subject. The device also includes a curved die at the distal end of the device for imparting a looping configuration to portions of the flexible elongated element exiting the distal end of the device, and a curved guide at the distal end of the device for receiving the looped flexible elongated element as it returns to the distal end of the device. In a further feature of the invention, a cutting mechanism is provided to permit the looped flexible elongated element to be separated from the remainder of the flexible elongated element. And in a further feature of the invention, the cutting mechanism is adapted to deform the trailing end of the looped flexible elongated element so that the trailing end is forced distally, toward the subject being sutured.

In another form of the invention, there is provided a suturing instrument for joining a first portion of material to a second portion of material, the suturing instrument comprising:

a handle;

an end effector mounted on the handle and defining therein:

a channel for supporting suture wire, the channel being curved to impart a looping configuration to portions of the suture wire passed therethrough;

an end recess adapted to receive the looped suture wire emerged from the channel; and a passageway for supporting a cutting bar, the passageway intersecting the channel so as to create an island between the channel and the passageway;

a wire advancing actuator mounted on the handle for moving the suture wire through the channel, through the material first and second portions and back into the end recess;

a cutting bar movably disposed in the passageway for selectively engaging the suture wire, the cutting bar being adapted to (1) cut the looped suture wire from the remaining portions of the suture wire; (2) bend the trailing end of the looped suture wire around the island; and (3) lift the looped suture wire over the island; and a cutting bar actuator mounted on the handle for moving the cutting bar into engagement with the suture wire.

In another form of the invention, there is provided a structure for supporting suture wire during driving of the suture wire, the structure comprising:

a first tube for closely surrounding and slidably supporting the suture wire;

a first pair of diametrically opposed openings formed in the first tube for exposing the suture wire for driving, the first pair of diametrically opposed openings being sized sufficiently small so as to maintain support for the suture wire;

a second tube disposed about a portion of the first tube; and a second pair of diametrically opposed openings formed in the second tube, the second pair of diametrically opposed openings being aligned with the first pair of diametrically opposed openings, and the second pair of diametrically opposed openings being sufficiently small so as to maintain support for the first tube.

In another form of the invention, there is provided a method for joining a first portion of material to a second portion of material, the method comprising:

providing a suturing instrument comprising:

a handle;

an end effector mounted on the handle and defining therein:

a channel for supporting suture wire, the channel being curved to impart a looping configuration to portions of the suture wire passed therethrough;

an end recess adapted to receive the looped suture wire emerged from the channel; and a passageway for supporting a cutting bar, the passageway intersecting the channel so as to create an island between the channel and the passageway;

a wire advancing actuator mounted on the handle for moving the suture wire through the channel, through the material first and second portions and back into the end recess;

a cutting bar movably disposed in the passageway for selectively engaging the suture wire, the cutting bar being adapted to (1) cut the looped suture wire from the remaining portions of the suture wire; (2) bend the trailing end of the looped suture wire around the island; and (3) lift the looped suture wire over the island; and a cutting bar actuator mounted on the handle for moving the cutting bar into engagement with the suture wire;

positioning the end effector against at least one of the portions to be joined;

moving the suture wire through the channel, through the material first and second portions and back into the end recess; and moving the cutting bar in the passageway so as to (1) cut the looped suture wire from the remaining portions of the suture wire; (2) bend the trailing end of the looped suture wire around the island; and (3) lift the looped suture wire over the island.

In another form of the invention, there is provided a method for driving wire, the method comprising the steps of:

providing a structure for supporting suture wire during driving of the suture wire, the structure comprising:

a first tube for closely surrounding and slidably supporting the suture wire;

a first pair of diametrically opposed openings formed in the first tube for exposing the suture wire for driving, the first pair of diametrically opposed openings being sized sufficiently small so as to maintain support for the suture wire;

a second tube disposed about a portion of the first tube; and a second pair of diametrically opposed openings formed in the second tube, the second pair of diametrically opposed openings being aligned with the first pair of diametrically opposed openings, and the second pair of diametrically opposed openings being sufficiently small so as to maintain support for the first tube; and engaging the suture wire with a pair of opposing rollers, each of the opposing rollers engaging the suture wire by accessing the suture wire through one of the second pair of diametrically opposed openings and one of the first pair of diametrically opposed openings.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 6-17 are various views showing various details of the suturing instrument's cannula assembly;

DETAILED DESCRIPTION OF THE PREFERRED EMBODIMENT

Overview

Figure 1:
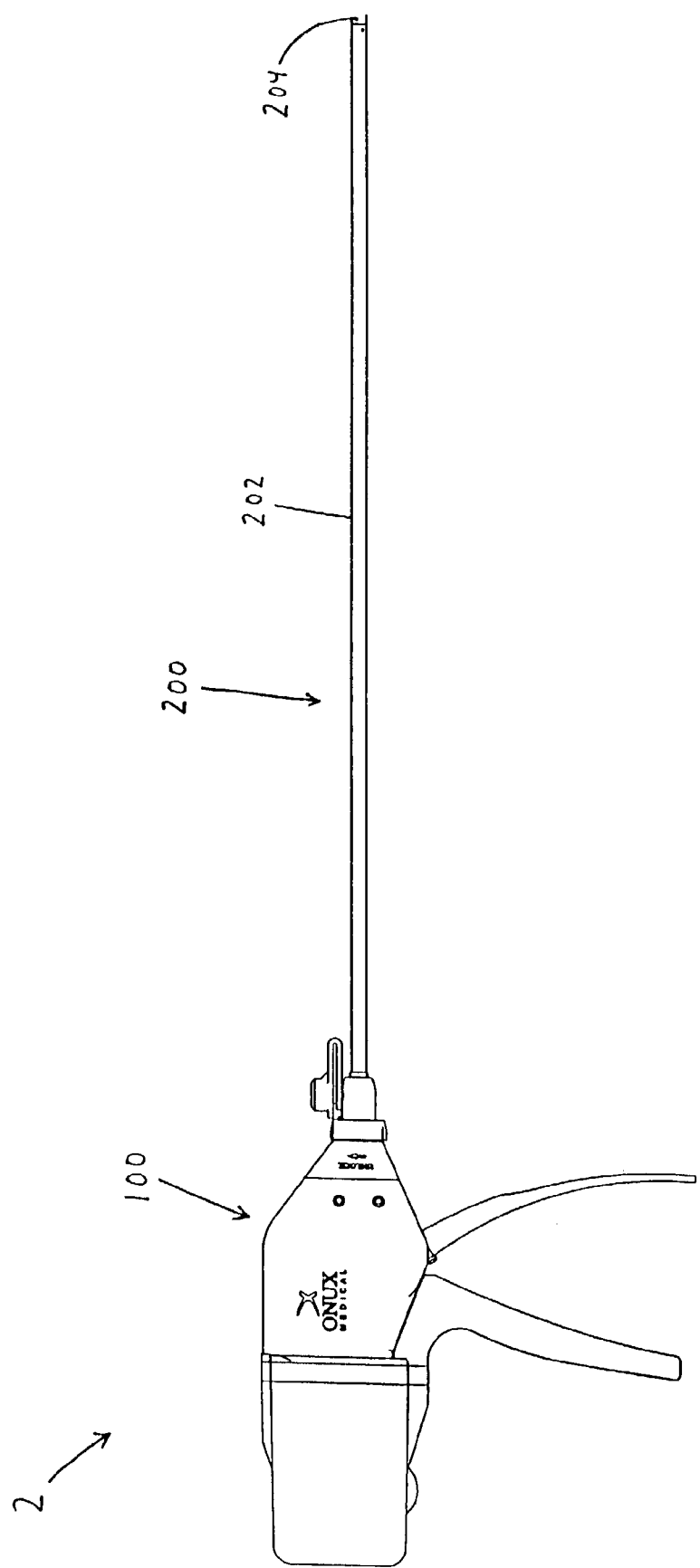
FIG. 1 is a side view showing a suturing instrument formed in accordance with the present invention.

Looking first at FIGS. 1-5, there is shown a suturing instrument 2 which comprises one preferred embodiment of the present invention. Suturing instrument 2 generally comprises a handle assembly 100, a cannula assembly 200, a wire drive assembly 300 (FIG. 5) and a wire supply cartridge 400, as will hereinafter be described in further detail.

Among other things, handle assembly 100 comprises a handle 102 and a lever 104, and cannula assembly 200 comprises a shaft 202, an end effector 204 and a wire cutting mechanism 206, as will also hereinafter be described in further detail.

As will be discussed in further detail below, generally during use, the suturing instrument's end effector 204 is positioned adjacent to the subject which is to be sutured. Then lever 104 is squeezed towards handle 102, causing wire drive assembly 300 to draw suture wire out of wire supply cartridge 400 and push the suture wire distally through cannula assembly 200 to end effector 204, where the suture wire exits the instrument with sufficient force to pass through the subject. End effector 204 includes a curved die for imparting a looping configuration to the portions of the suture wire exiting the distal end of the instrument, and a curved guide for receiving the looped suture wire as it returns to the distal end of the instrument. The looped suture wire may then be cut off, at end effector 204, from the remaining suture wire that extends back through the suturing instrument. Such cutting is preferably automatically effected by wire cutting mechanism 206 at the conclusion of the lever's stroke.

As will be discussed in further detail below, wire supply cartridge 400 may be supplied separately from suturing instrument 2, with wire supply cartridge 400 being loaded into suturing instrument 2 prior to commencing a suturing operation. As will also be discussed in further detail below, wire supply cartridge 400 may be disposable, such that the cartridge may be discarded after use.

Handle Assembly 100

Still looking at FIGS. 1-5, handle assembly 100 comprises a housing 106, with the aforementioned handle 102 being fixedly attached to housing 106 and the aforementioned lever 104 being pivotally connected to housing 106 by a pivot pin 108.

The inner end of lever 104 includes a slot 110 for receiving a roll pin 112 therein. Roll pin 112 is also secured to a rack 114. Rack 114 is connected to a compression spring 116 at its distal end. Rack 114 includes a length of teeth 118 intermediate to its length, followed by a smooth wall 120 adjacent to its proximal end. As a result of this construction, compression spring 116 normally biases rack 114 proximally, so that lever 104 is biased away from handle 102; however, lever 104 may be squeezed toward handle 102 so as to overcome the force of spring 116, whereby to move rack 114 distally. A pawl 122 (FIG. 3), riding on lever 104 and engaging a set of teeth 124, ensures that lever 104 cannot return to its proximal starting position without moving through one complete stroke. A removable shroud 126 selectively closes off the proximal end of housing 106. The removable nature of shroud 126 permits a fresh wire supply cartridge 400 to be loaded into the suturing instrument and an exhausted wire supply cartridge to be removed from the instrument, as will hereinafter be discussed in further detail.

Cannula Assembly 200

Cannula assembly 200 is shown in greater detail in FIGS. 6-16. As noted above, cannula assembly 200 (FIG. 2) comprises shaft 202, end effector 204 and wire cutting mechanism 206.

More particularly, shaft 202 comprises a tube 208 having a distal end 210 and a proximal end 212. A mount 214 is secured to tube 208 near its proximal end whereby shaft 202, and hence the entire cannula assembly 200, may be removably attached to housing 106 of handle assembly 100. Mount 214 includes a flushing port 216 (FIG. 7), communicating with the interior of tube 208 via an opening 218 (FIG. 8), for cleaning the interior of cannula assembly 200. A cap 220 selectively closes off flushing port 216.

End effector 204 is secured to the distal end of tube 208.

End effector 204 is configured so as to form a modified suture loop 422 (FIG. 26), sometimes referred to as a "suture clip" or a "Q-form loop" or a "Q-form clip", as will hereinafter be discussed.

Figure 10:
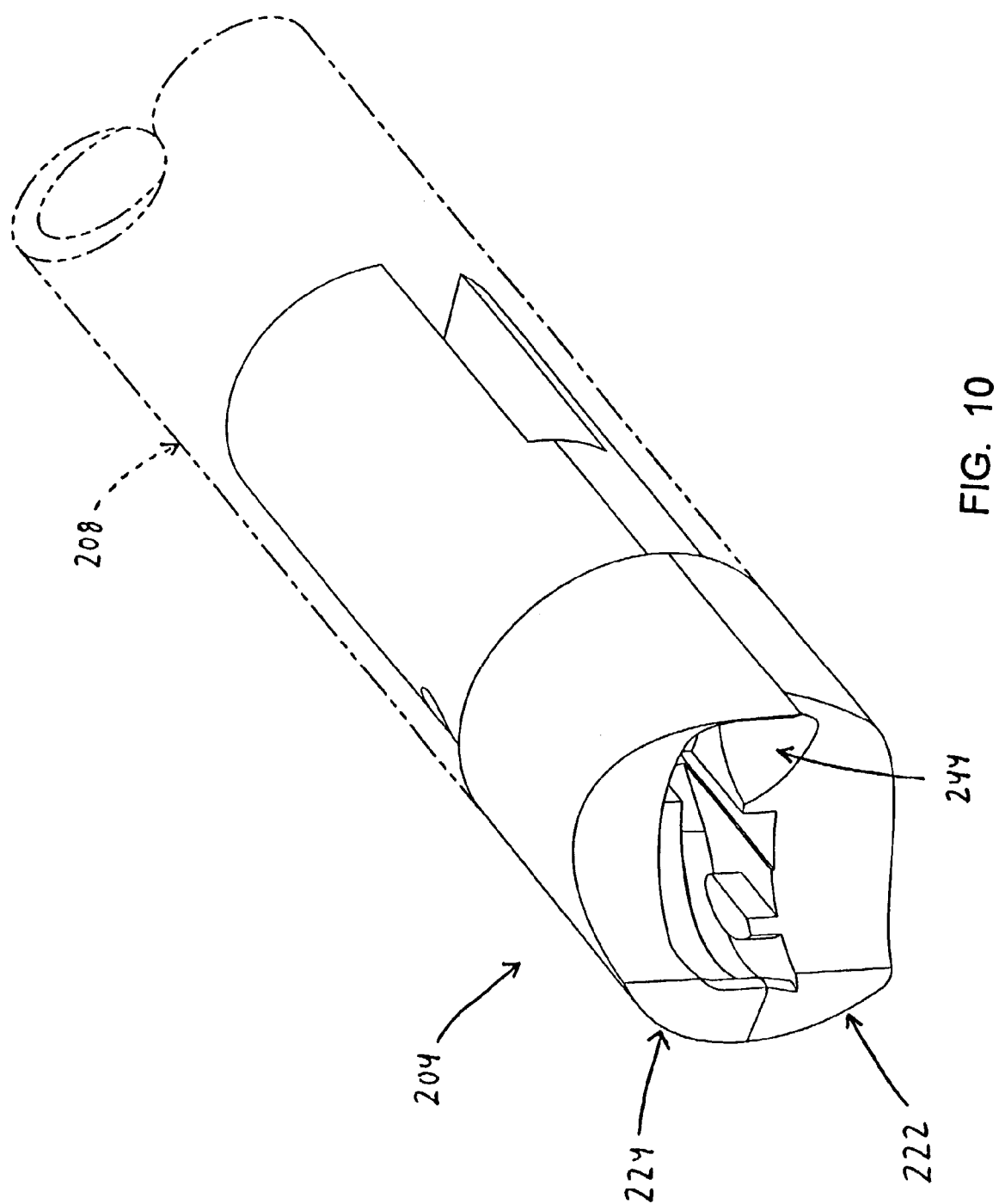
Figure 11:
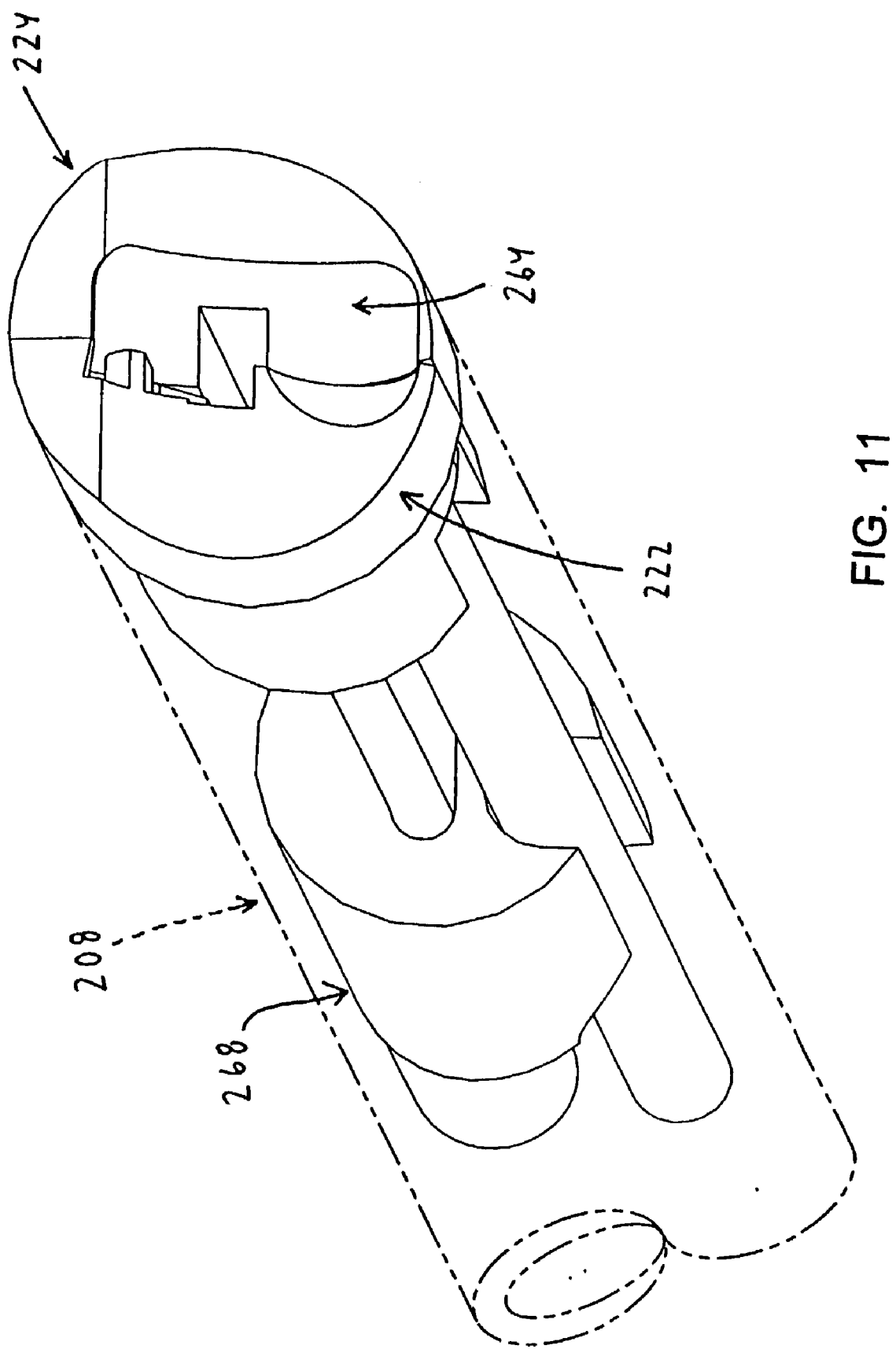
Figure 17:
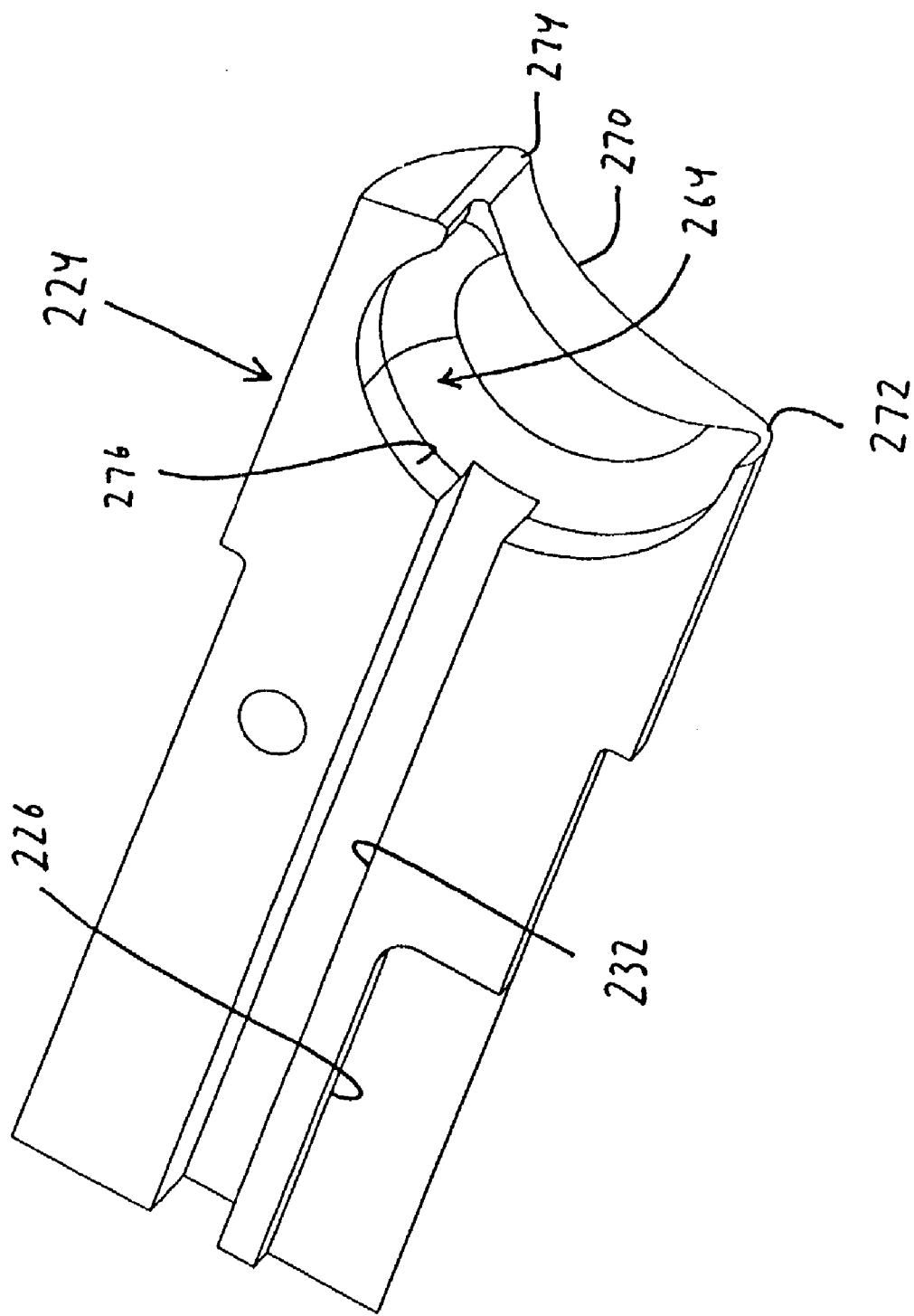
Figure 18:
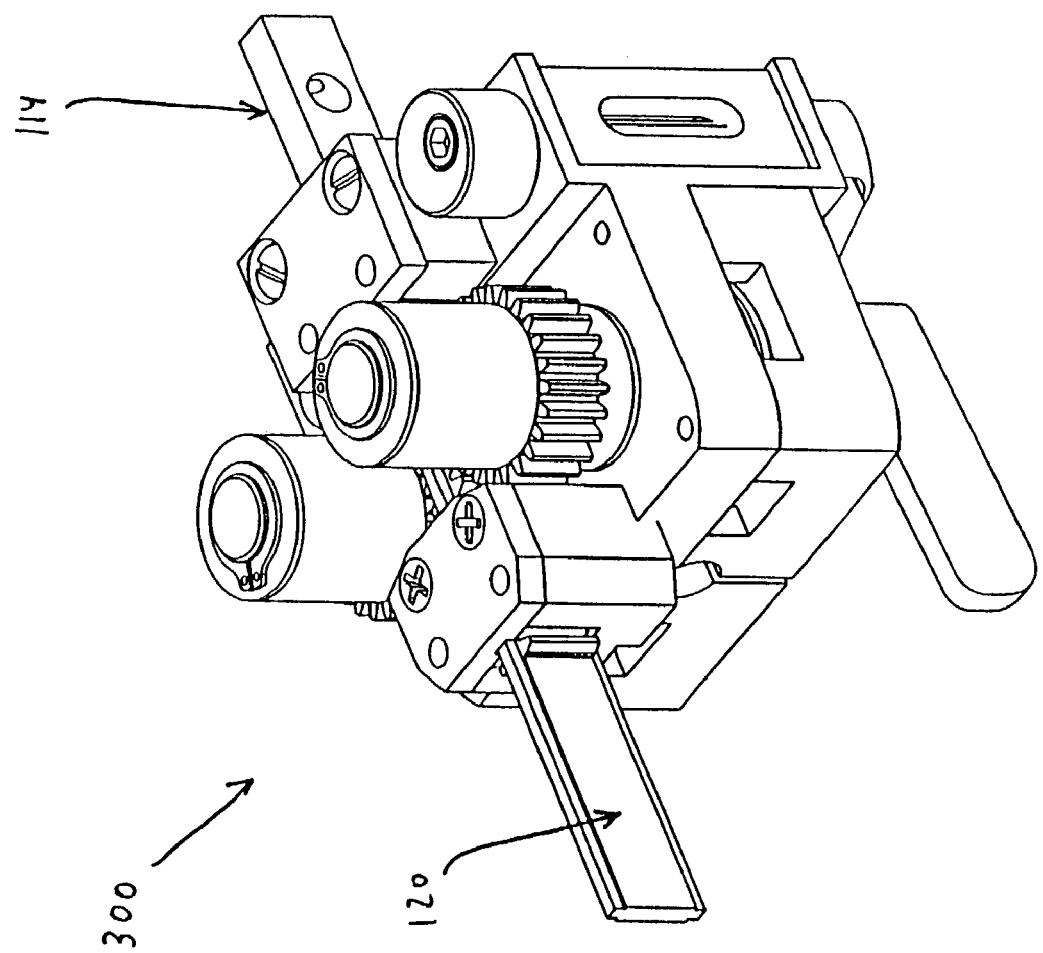
FIGS. 18-21 are various views showing various details of the suturing instrument's wire drive assembly.
Figure 19:
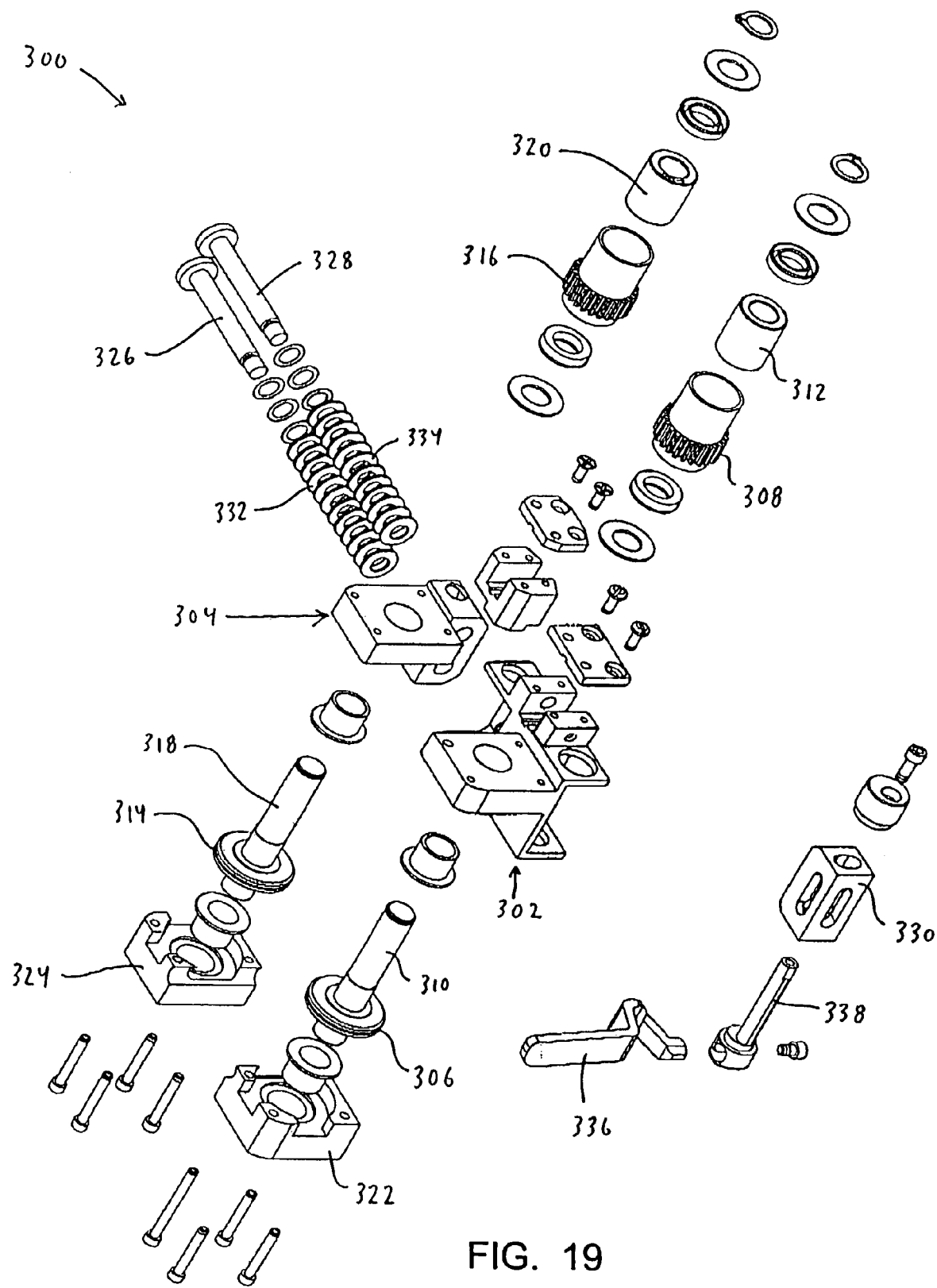
Figure 20:
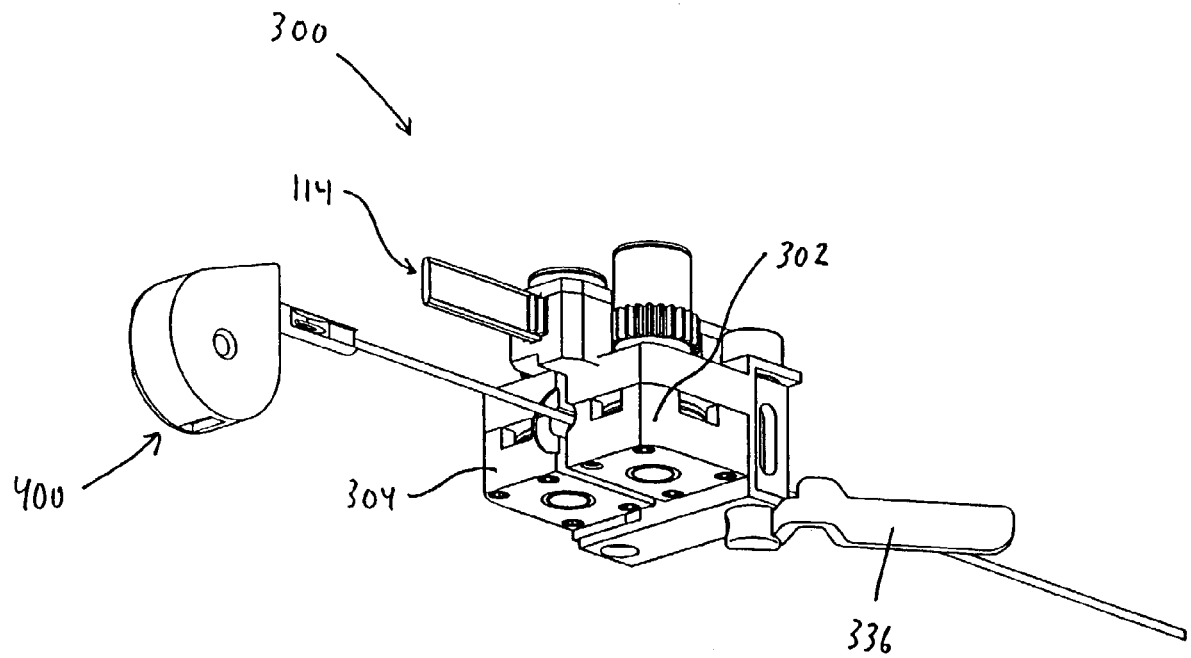
Figure 21:
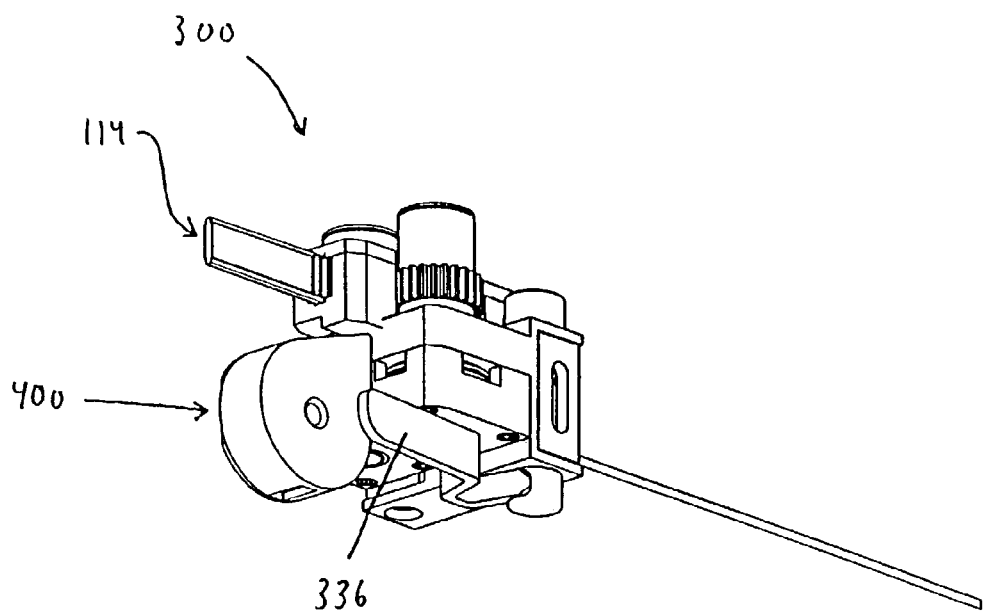
Figures 22, 23:
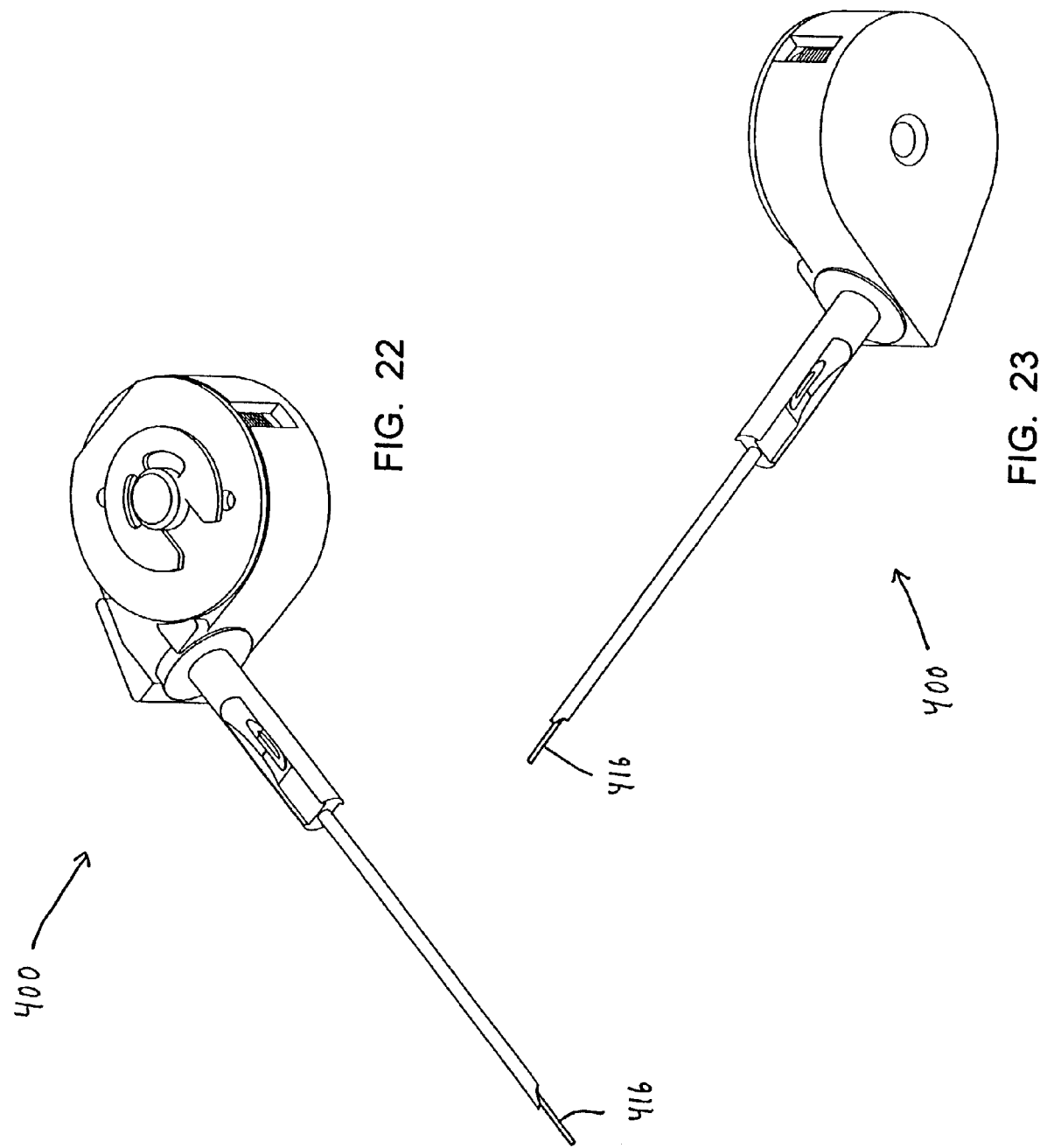
FIGS. 22-25 are various views showing various details of the suturing instrument's wire supply cartridge.
Figure 24:
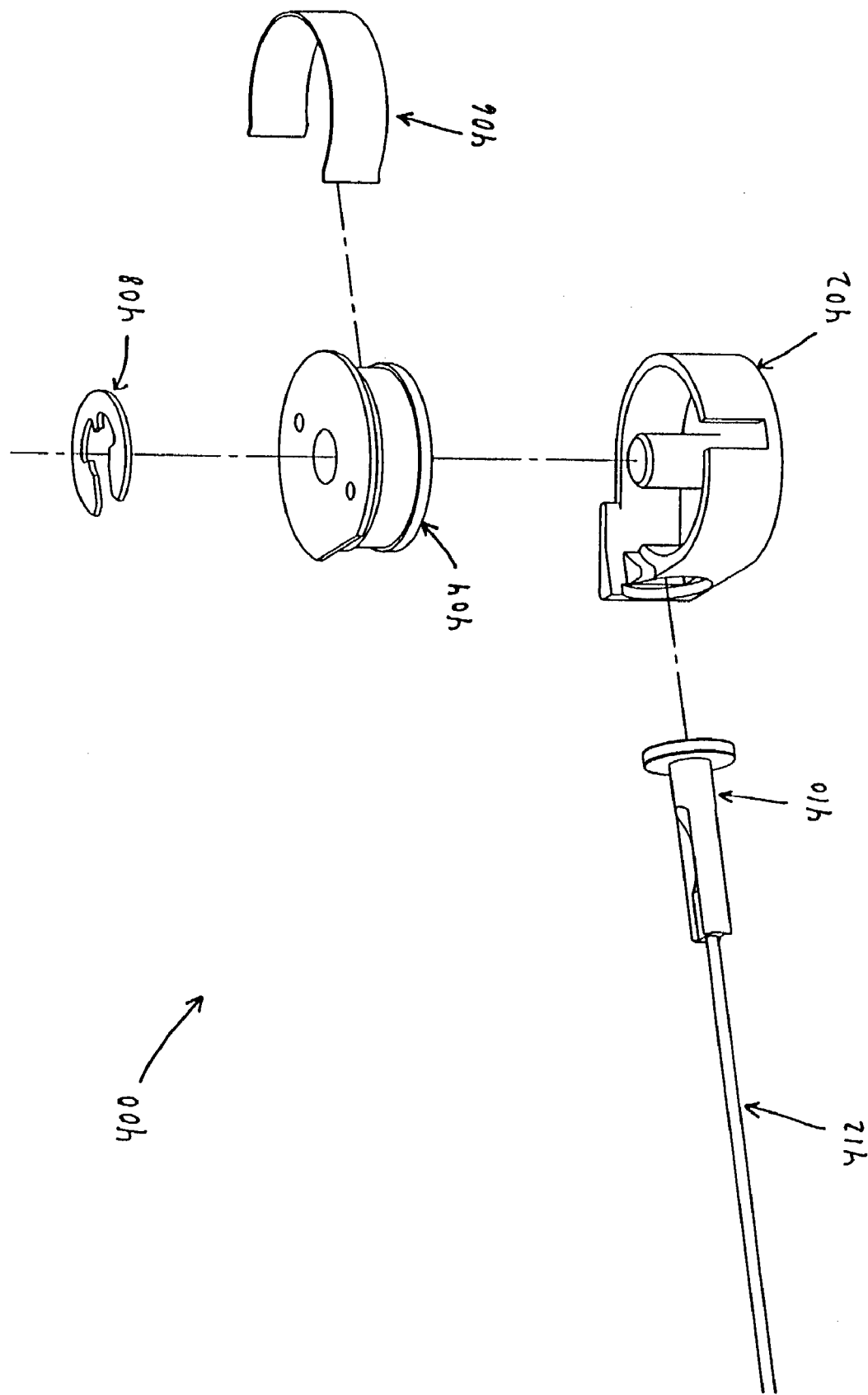
Figure 25:
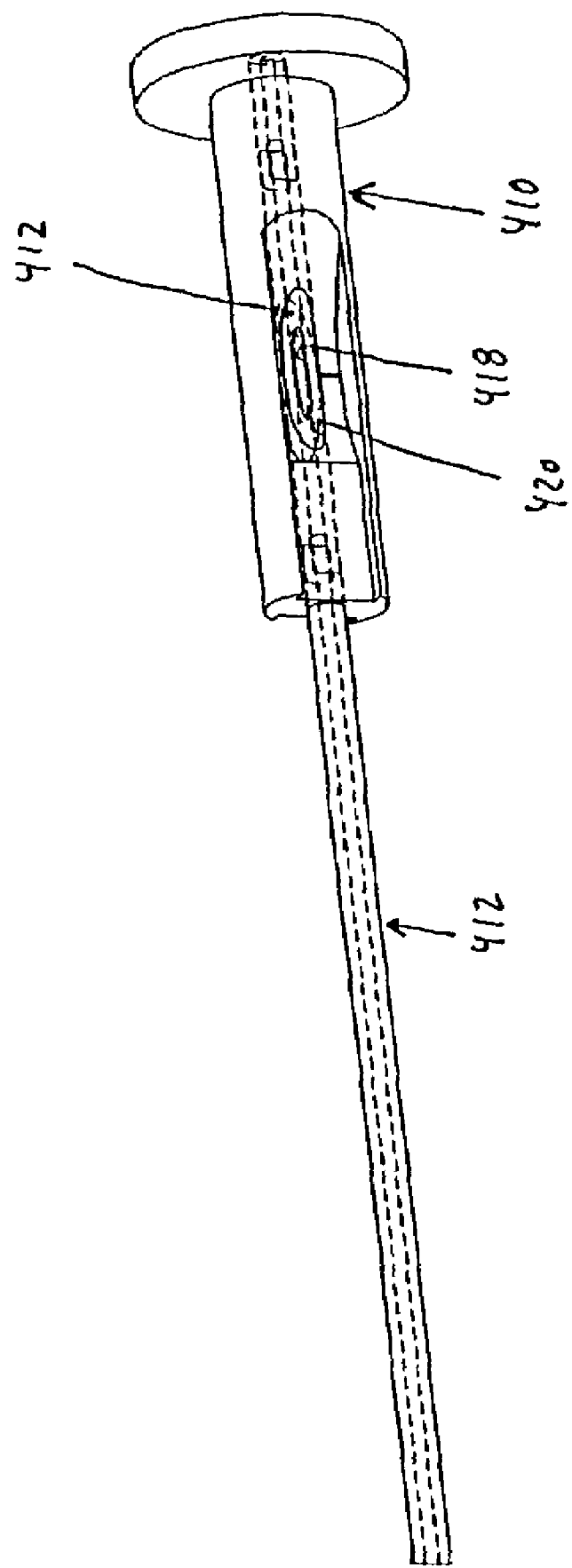

More particularly, end effector 204 comprises a fixed first portion 222 (FIGS. 10, 11 and 12) and a fixed second portion 224 (FIGS. 10, 11, and 17).

Figure 12:
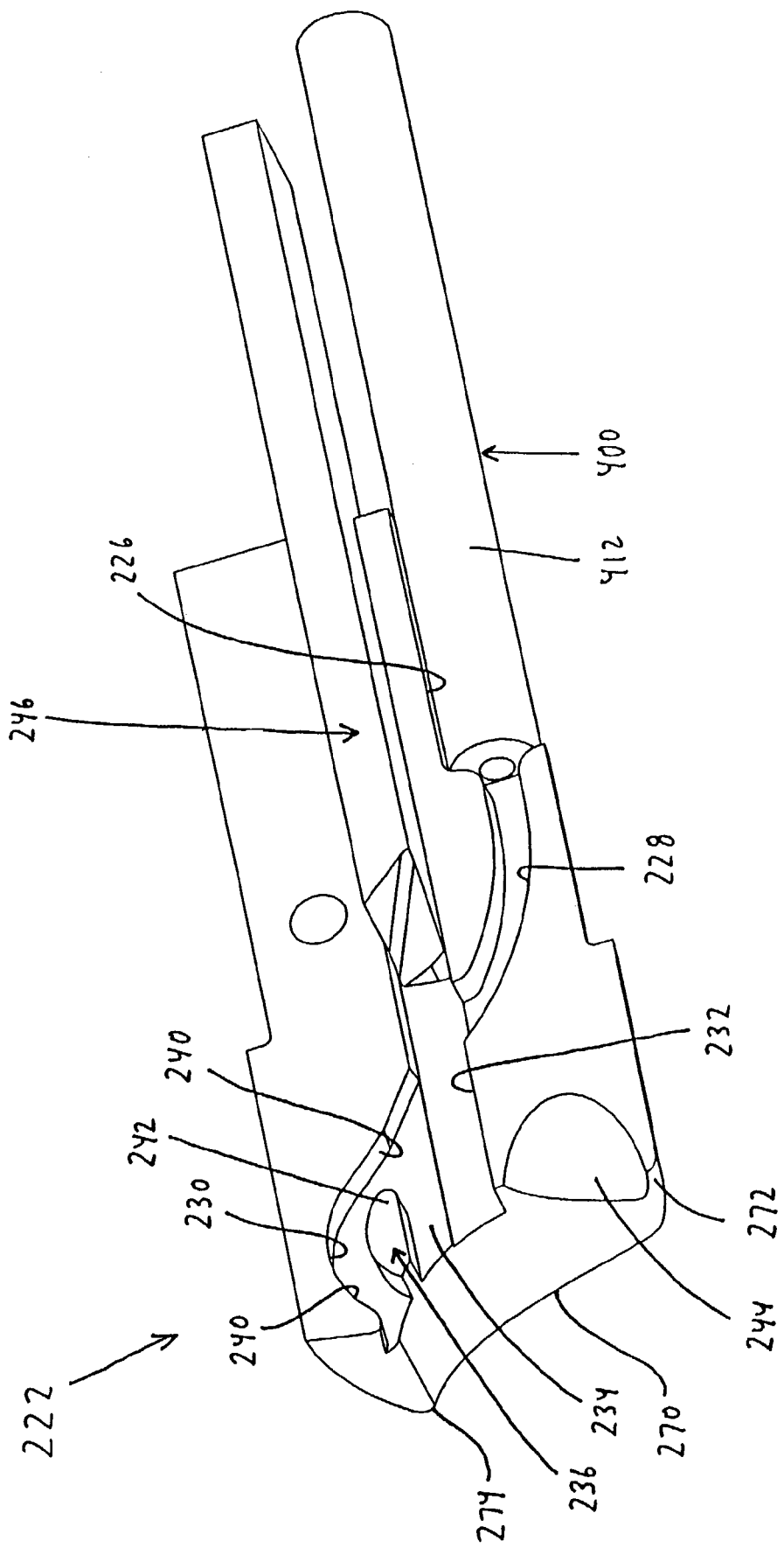

As seen in FIG. 12, fixed first portion 222 includes a first channel 226 for receiving the distal end of the aforementioned wire supply cartridge 400, a smaller diameter second channel 228 for supporting suture wire as the suture wire emerges from wire supply cartridge 400, and a third channel 230 for receiving the suture wire after the suture wire passes by cutting bar channel 232 and for imparting a selected curvature to the suture wire, whereby to form the suture loop, as will hereinafter be discussed in further detail. Second channel 228 and third channel 230 are coplanar. In addition to the foregoing, material is removed from fixed first portion 222 at the location 234 so as to effectively form an island 236 at the distal end of end effector 204.

Figure 13:
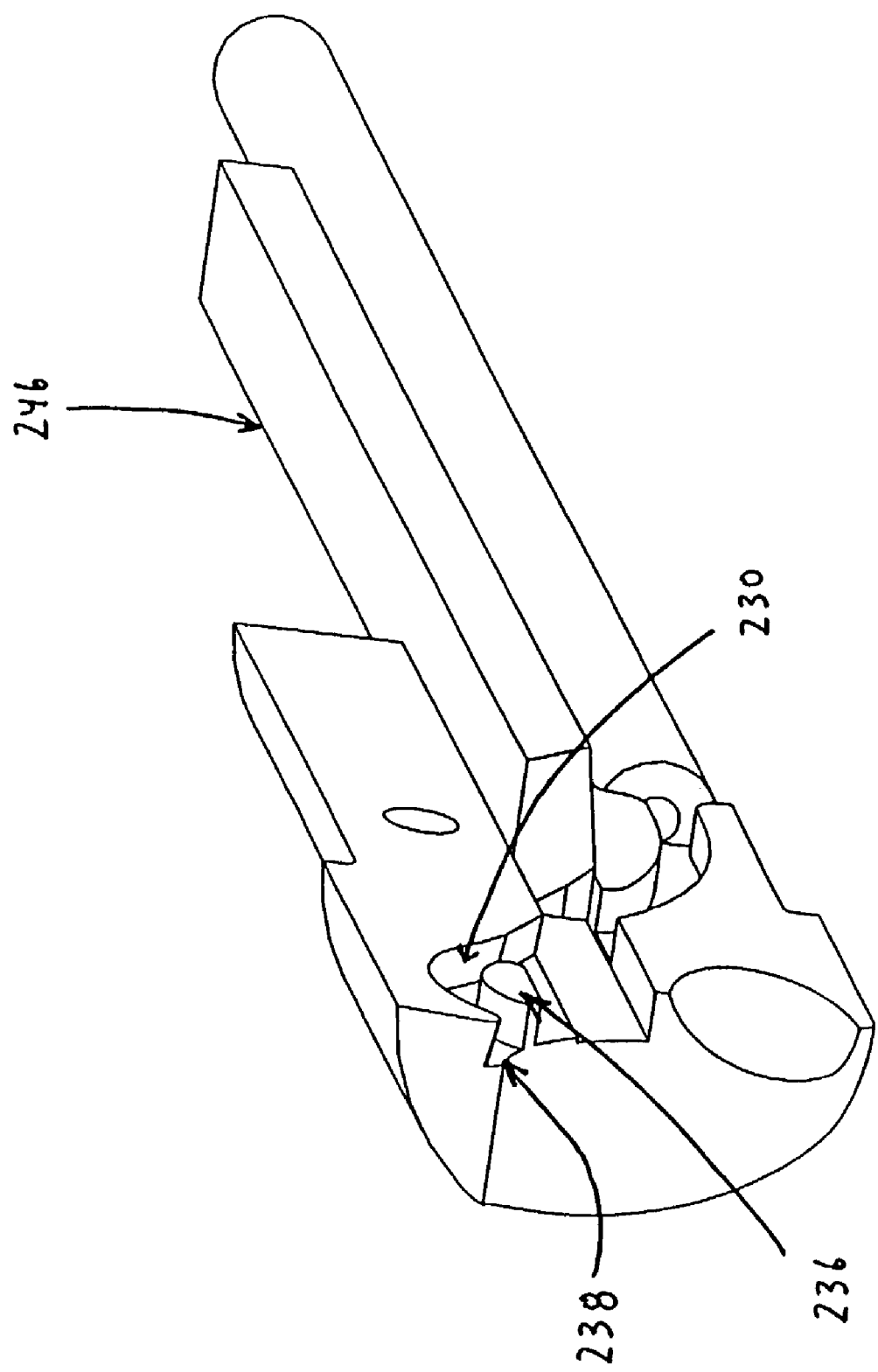
Figure 14:
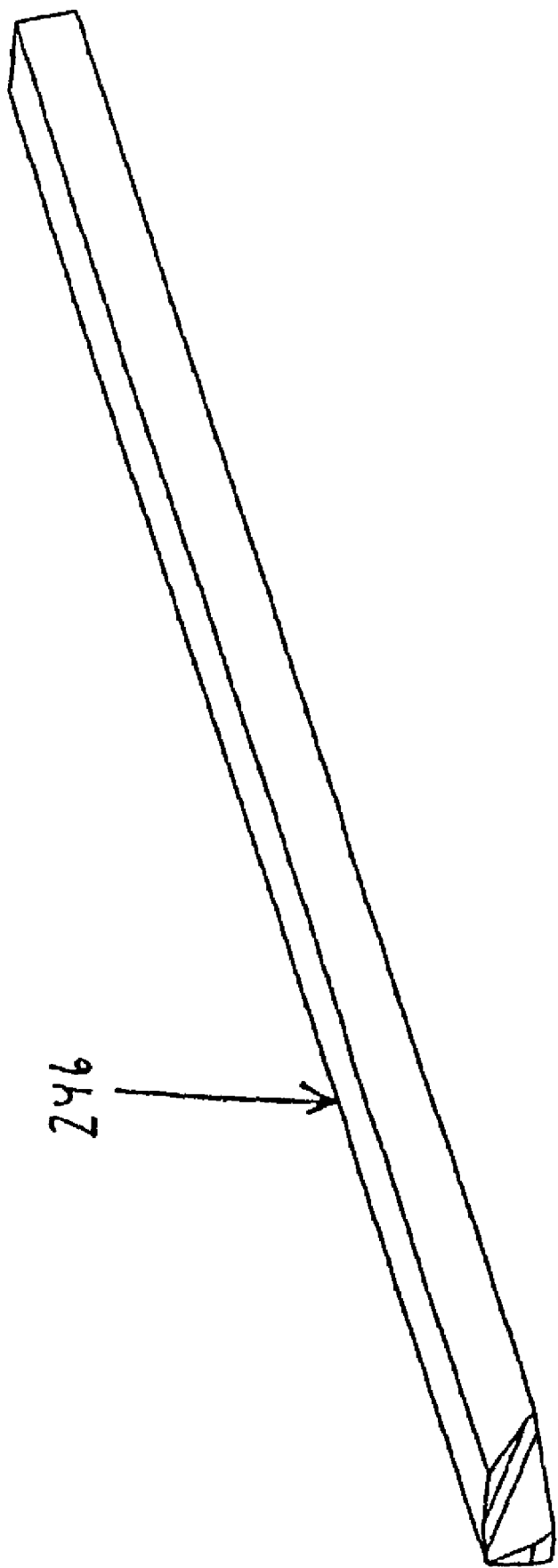
Figure 15:
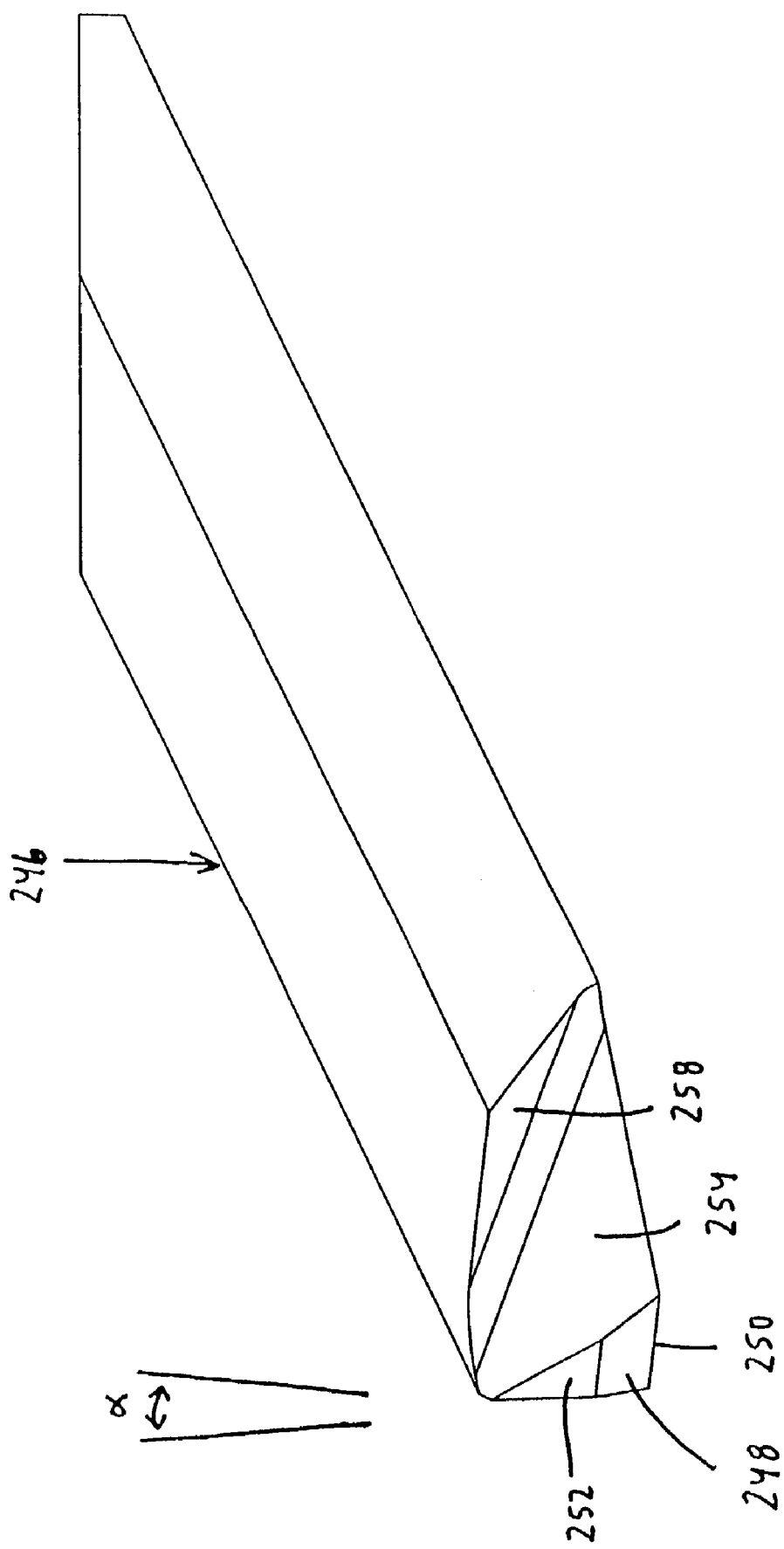
Figure 16:
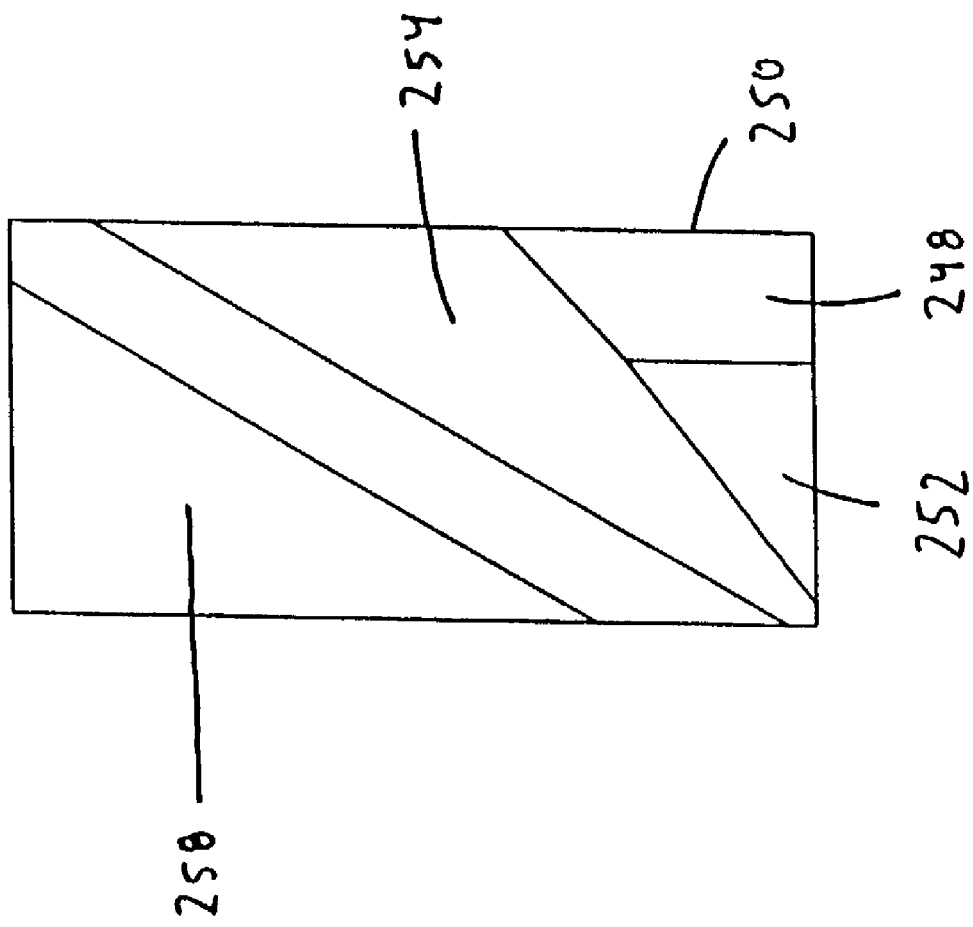

In order to assist the controlled retention of suture wire during its travel within second channel 228 and third channel 230, one or both of these channels may be given an undercut profile such as the dovetail profile 238 shown in FIG. 13 with respect to third channel 230. At the same time, in order to minimize harmful friction between the suture wire and fixed first portion 222, second channel 230 may be widened slightly at locations other than 240 (FIG. 12); locations 240 are, for this particular clip form, the operative contact points for effecting wire bending (in this respect it should be appreciated that other particular clip forms may have other contact points). In addition, in order to facilitate the release of a formed suture clip from the instrument, the proximal end of island 236 may be relieved slightly at 242 (FIG. 12).

In addition to the foregoing, fixed first portion 222 may be relieved as shown as 244 (FIG. 10) so as to form a curved guide at the distal end of the instrument for receiving the looped suture wire as it returns to the distal end of the instrument.

Figure 2:
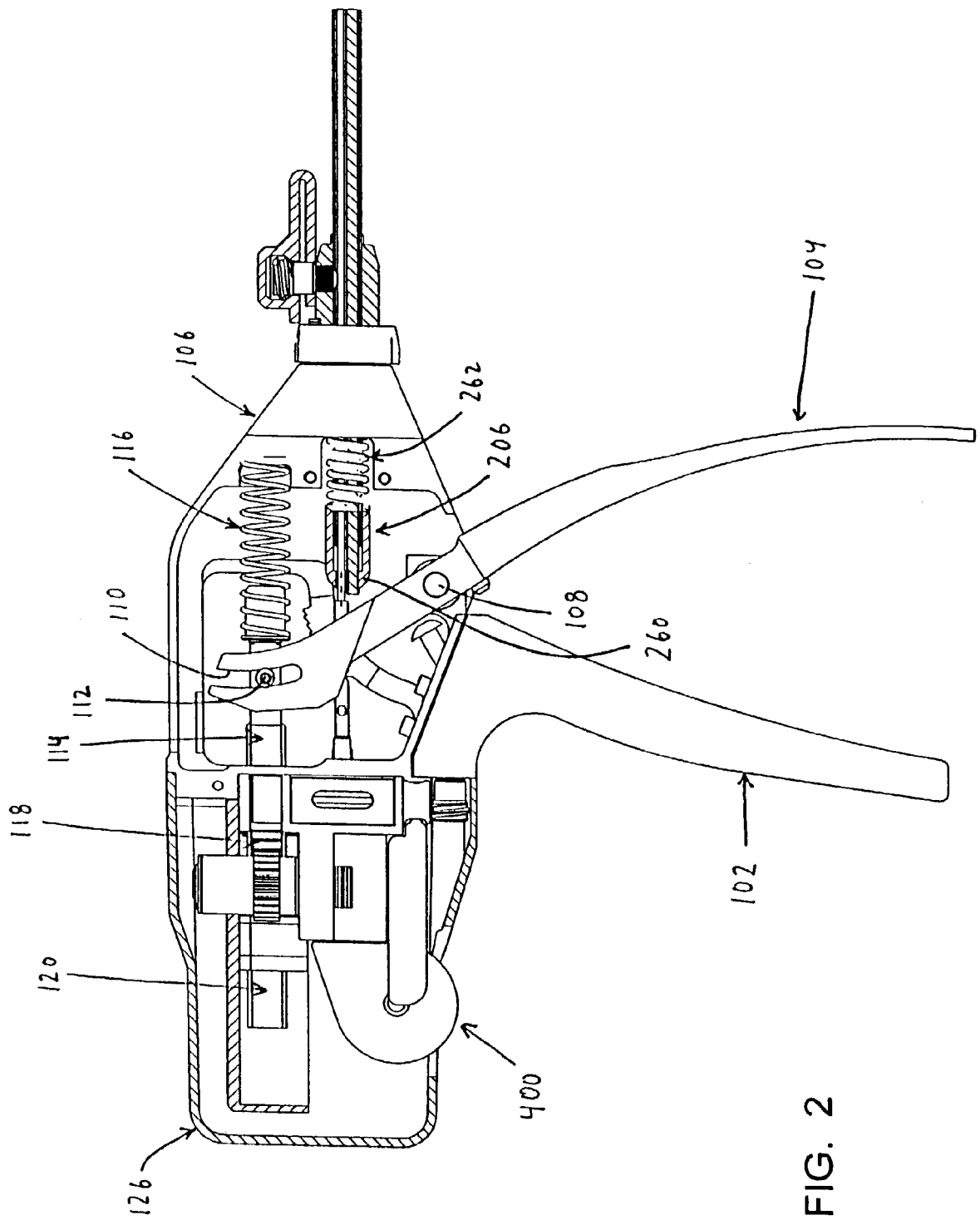
FIGS. 2-5 are various views showing various details of the suturing instrument's handle assembly.
Figure 3:
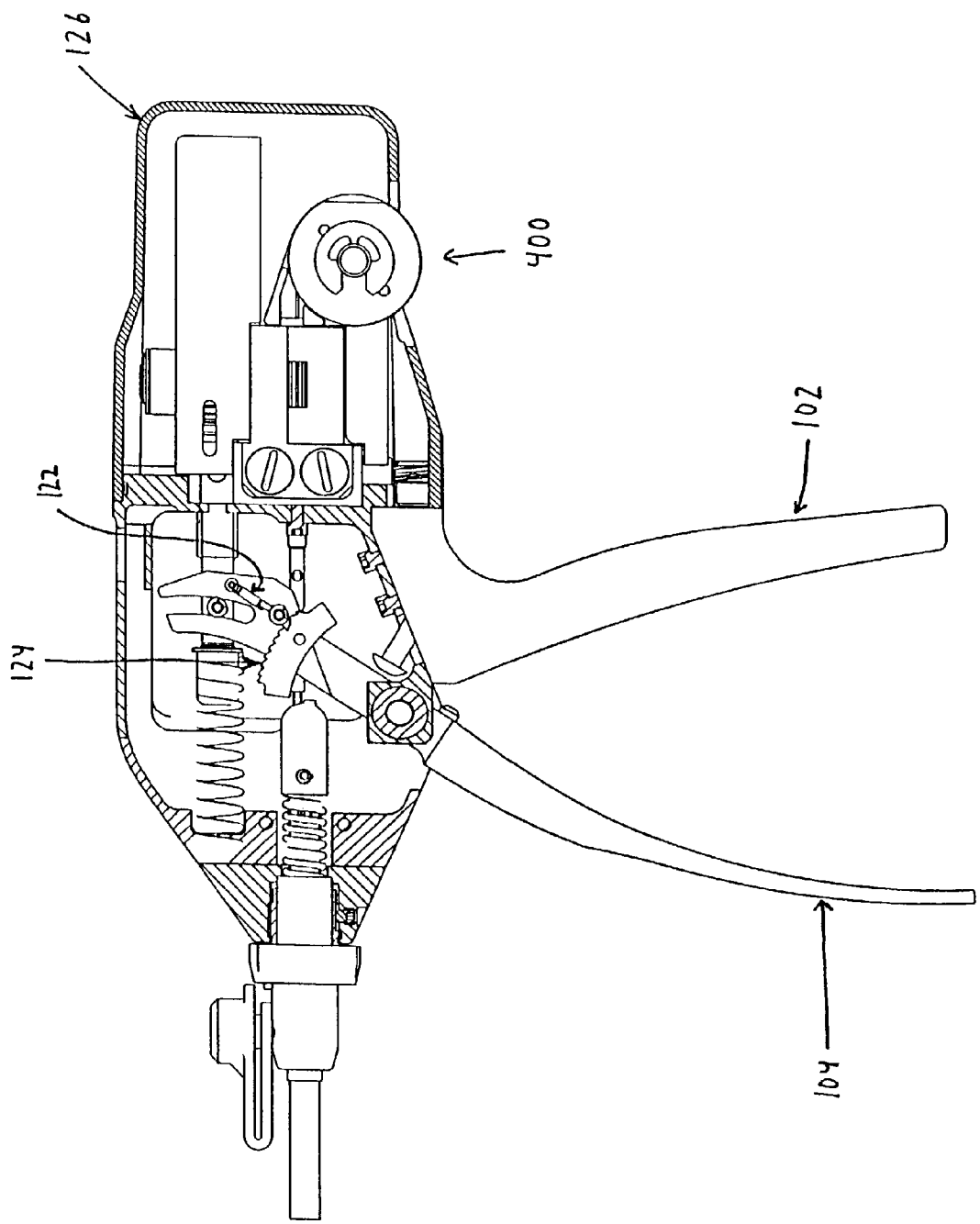
Figures 4A, 4B:
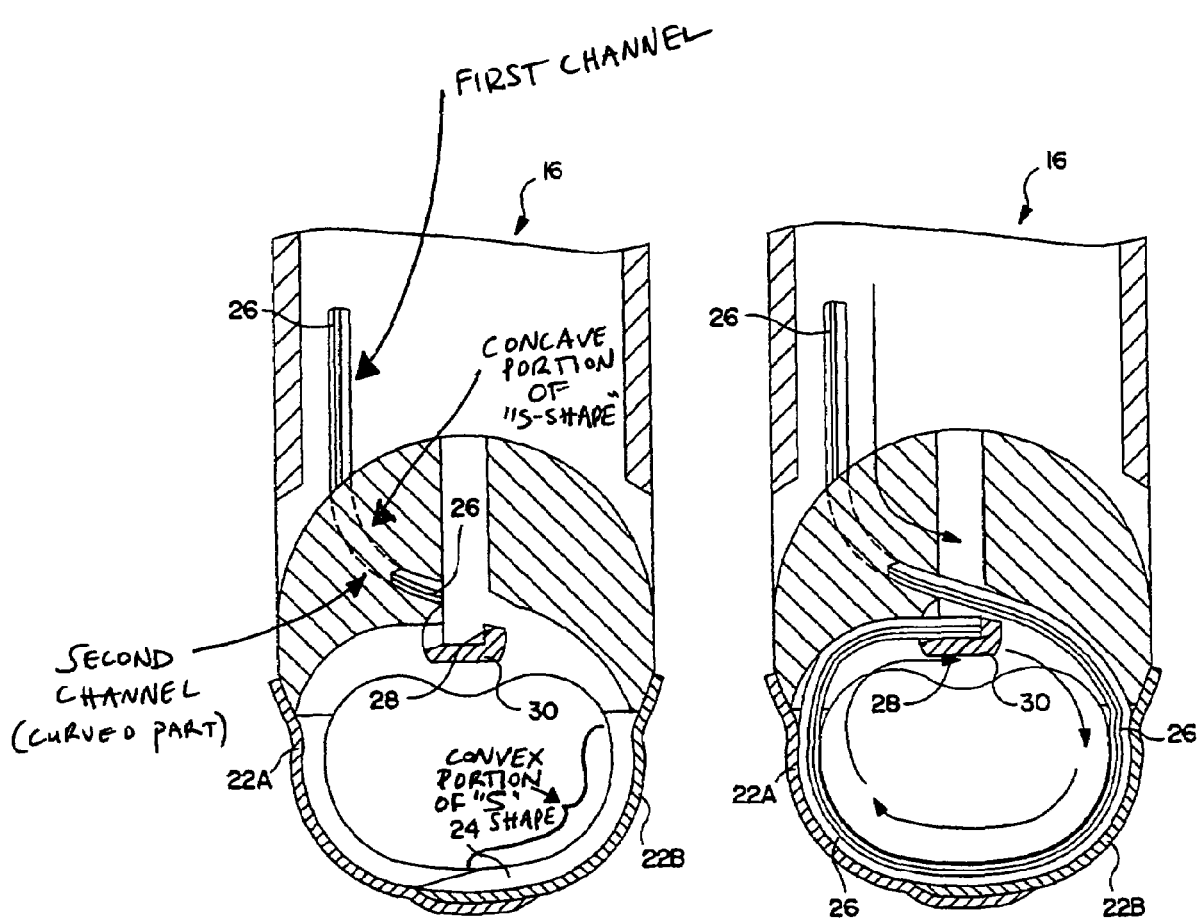
Figure 5:
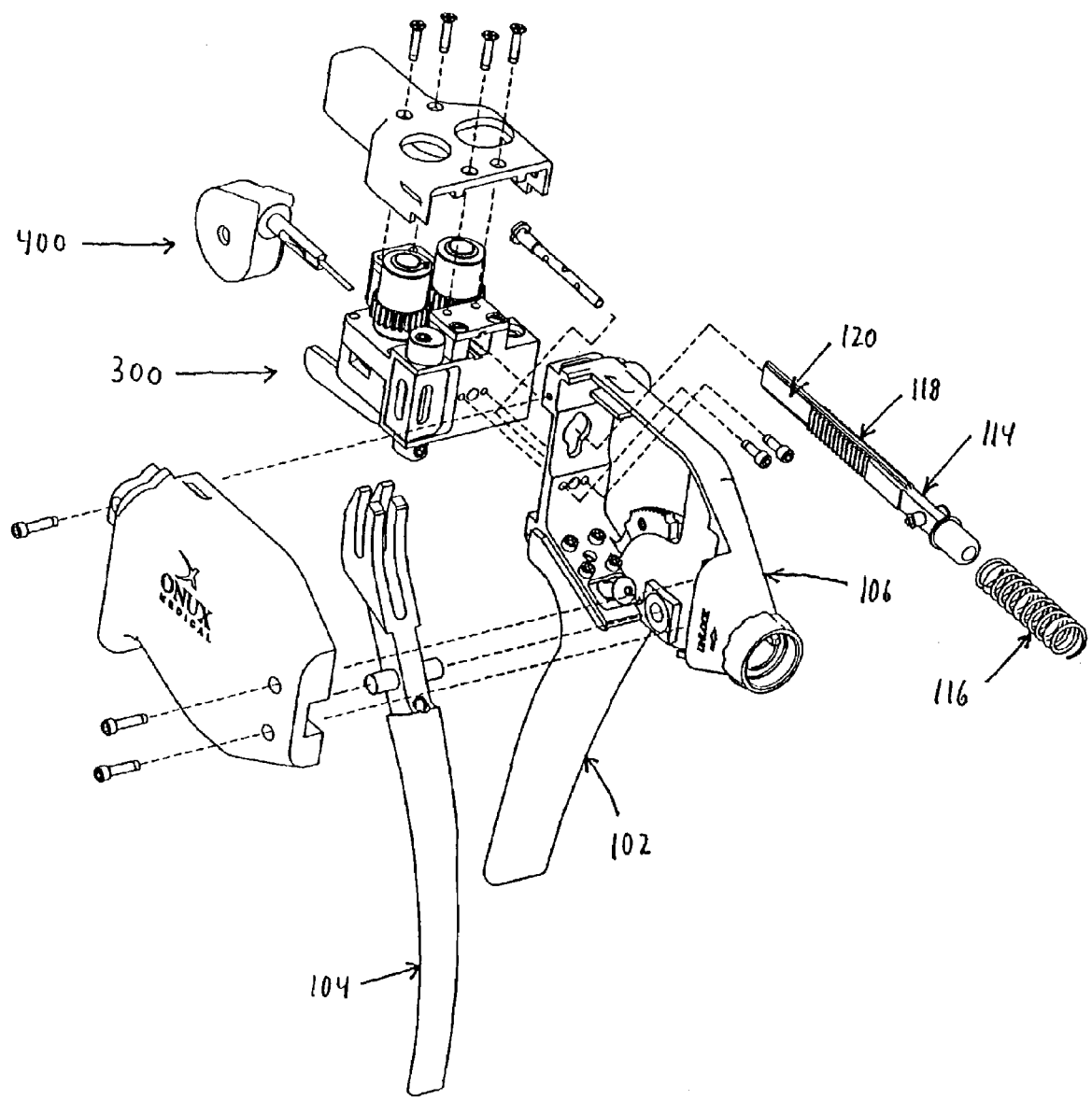
Figure 6:
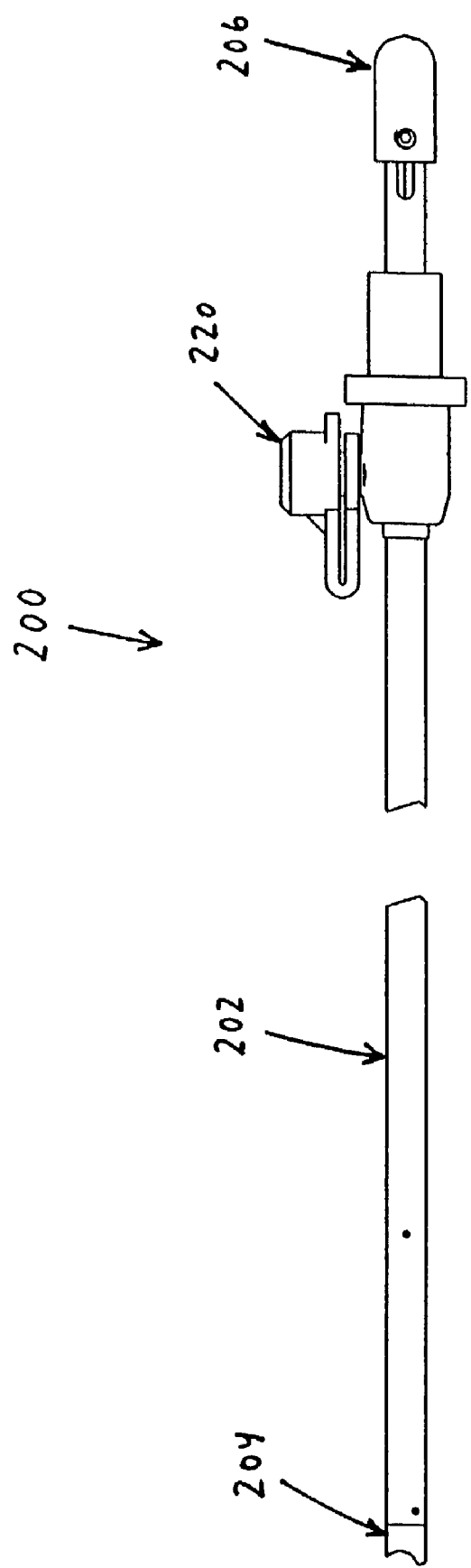
Figure 9:
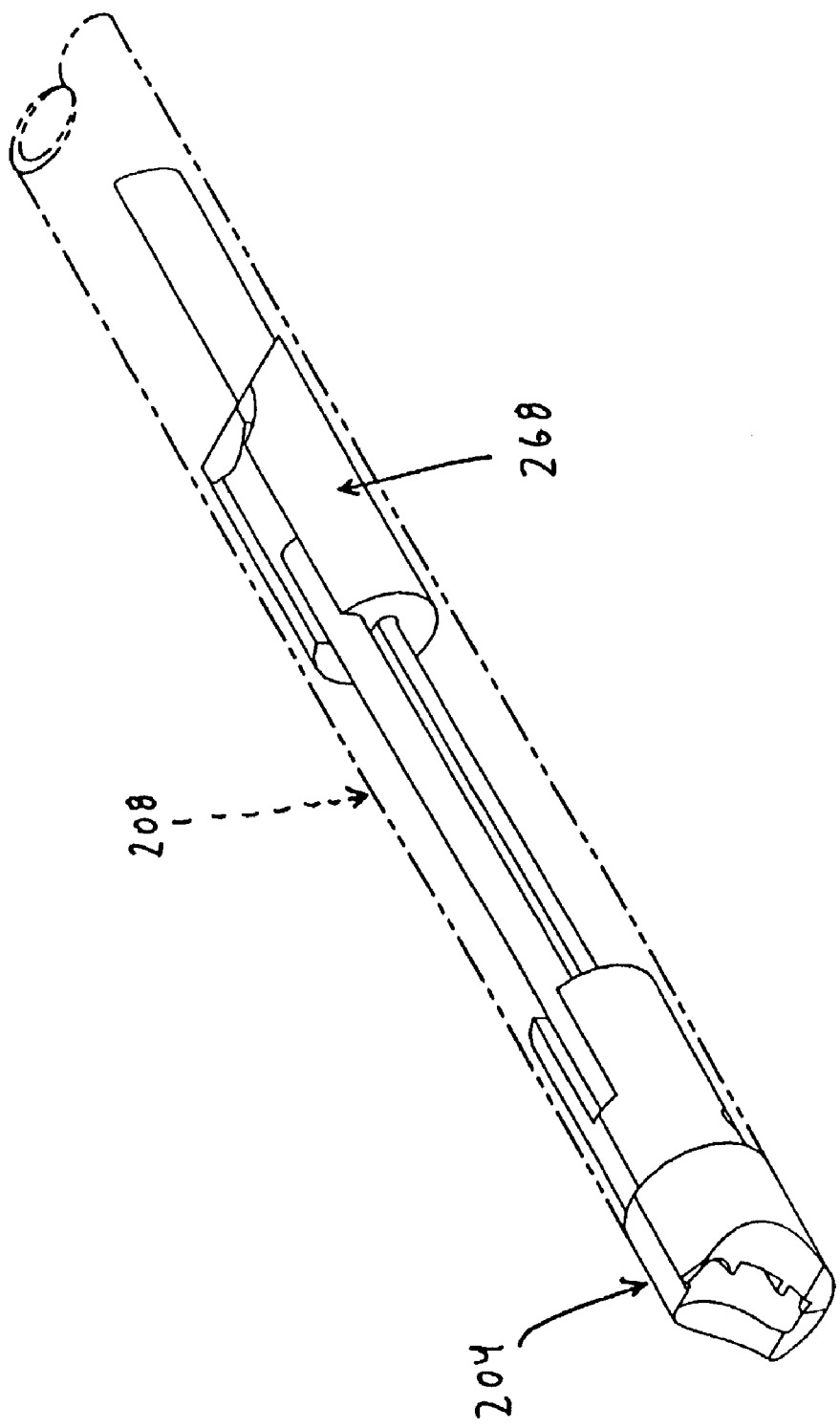

Wire cutting mechanism 206 comprises a cutting bar 246 (FIGS. 2, 12 and 14-16). The distal end of cutting bar 246 is disposed in the aforementioned cutting bar channel 232 (FIG. 12) and the proximal end of cutting bar 246 protrudes from the proximal end 212 of tube 208 (FIGS. 2 and 8).

The distal end of cutting bar 246 (FIGS. 12, and 14-16) preferably comprises a plurality of distinct faces, i.e., a cutting face 248 defining a cutting edge 250, a relief face 252 set at an angle α to cutting face 248, an ejection ramp face 254, and an ejection push face 258. As will hereinafter be discussed in further detail, when cutting bar 246 is driven distally so as to encounter suture wire extending between second channel 228 and third channel 230 (and hence across cutting bar channel 232), cutting edge 250 will sever the suture wire, ejection ramp face 254 will lift the trailing end of the severed suture wire out of cutting bar channel 232 and up over island 236 so that the loop may be released from the distal end of the suturing instrument, and ejection push face 258 will push the suture loop free from the distal end of suturing instrument 2.

The proximal end of cutting bar 246 comprises a pusher element 260 (FIGS. 2 and 8) adapted to be engaged by lever 104 when cannula assembly 200 is mounted to handle assembly 100 and lever 104 is pulled toward handle 102, whereby to move cutting bar 246 distally within cannula assembly 200. A compression spring 262 is located between pusher element 260 and mount 214 so as to bias cutting bar 246 proximally. As will hereinafter be discussed in further detail, the operations of lever 104 and wire cutting mechanism 206 are preferably coordinated with one another so that pusher element 260 is not engaged by lever 104 until the later part of the lever's stroke, so that advancement of the suture wire will have ceased by the time cutting bar 246 is activated.

Looking next at FIGS. 10, 11 and 17, fixed second portion 224 includes the second half of the aforementioned first channel 226 for receiving the distal end of the aforementioned wire supply cartridge 400, the second half of the aforementioned cutting bar channel 232, and a slot 264 which extends proximally from the distal end of the instrument. Slot 264 is sized so that when first fixed portion 222 is engaging second fixed portion 224, a gap slightly wider than the diameter of the suture wire will be formed between the top of island 236 and the opposing material of fixed second portion 224, in order to permit a formed loop of suture wire to be released from the end of the suturing instrument, as will also hereinafter be discussed in further detail. Slot 264 is configured so that the suture wire will be maintained in third channel 230 until after the suture wire has been cut and partially bent so as to keep the suture wire in position for proper cutting and bending.

Fixed first portion 222 and fixed second portion 224 are preferably formed out of material which is harder than the suture wire passing through channels 228 and 230, so as to minimize wear on the instrument. In one preferred form of the invention, first fixed portion 222 and fixed second portion 224 are formed out of a carbide alloy.

Preferably a loading guide 268 (FIGS. 8, 9 and 11) is positioned in tube 208 between end effector 204 and mount 214, so as to provide guidance and support for cutting bar 246 and the distal end of wire supply cartridge 400.

In one preferred form of the invention, end effector 204 includes a recess 270 (FIGS. 12 and 17) at its front end. Recess 270 permits soft tissue to protrude into the interior of end effector 204 (see FIG. 27) and provides a pair of projections 272, 274 for pressing into the tissue and stabilizing the suturing instrument thereagainst. If desired, one or both of the projections 272, 274 can be made relatively sharp so as to enhance tissue engagement or manipulation of prosthetic material (e.g., surgical mesh), and/or one of the projections (e.g., projection 274) can be made slightly longer than the other projection, so as to facilitate an oblique approach to a tissue surface (see, for example, FIG. 26).

Wire Drive Assembly 300

Looking next at FIGS. 4, 5 and 18-21, wire drive assembly 300 comprises a fixed block 302, a movable block 304, a first drive shaft roller 306 connected to a spur gear 308 via an axle 310 passing through fixed block 302 and a one way clutch 312, and a second drive shaft roller 314 connected to a spur gear 316 via an axle 318 and a one way clutch 320. A pair of capture blocks 322 and 324 rotatably capture drive shaft rollers 306 and 314 to blocks 302 and 304, respectively.

Movable block 304 is slidably mounted to fixed block 302 via a pair of rods 326 and 328 that pass through movable block 304, fixed block 302 and are secured to a cam follower 330, with springs 332 and 334 biasing movable block 304 into engagement with fixed block 302. A lever 336 and cam 338 are provided for manually forcing movable block 304 away from fixed block 302, and hence drive shaft roller 314 away from drive shaft roller 306, and hence spur gear 316 away from spur gear 308.

Wire drive assembly 300 is normally disposed in handle assembly 100 so that spur gear 308 and 316 engage the teeth 118 of rack 114, and so that drive shaft roller 314 is in substantial engagement with drive shaft roller 306.

However, depressing lever 336 will cause cam follower 338 to pivot, whereby to force movable block 304 away from fixed block 302 and whereby to separate roller 314 from roller 306 (and to separate spur gear 316 from spur gear 308). Wire supply cartridge 400 may then be inserted between rollers 314 and 306 and, by then restoring lever 336 to its inboard position, cause the suture wire to be gripped by rollers 306 and 314, whereupon the suture wire may be driven by rollers 306 and 314 out the distal end of the suturing instrument.

More particularly, after a fresh wire supply cartridge 400 has been installed in the instrument, suture wire may be driven out the distal end of the instrument by depressing lever 104 toward handle 102. Depressing lever 104 toward handle 102 causes roll pin 112 (FIG. 2) to ride within slot 110. More particularly, as the top end of lever 104 moves about pivot pin 108, roll pin 112 moves through slot 110. This causes rack 114 to move distally, which in turn causes spur gears 308 and 316 to rotate, which in turn causes rollers 306 and 314 to rotate, which in turn causes a length of suture wire to be advanced out the distal end of the suturing instrument.

As lever 104 continues to rotate, the toothless region of rack 114 (i.e., the smooth wall 120 at the proximal end of rack 114) is advanced to spur gears 308 and 316, whereby rotation of rollers 306 and 314 will cease and suture wire will no longer be advanced out the distal end of the suturing instrument. Thus it will be seen that by carefully regulating the length of the rack's teeth 118, the length of suture wire ejected from the instrument can also be regulated.

Further movement of lever 104 will then cause the cutting bar's pusher element 260 (FIG. 2) to be engaged, whereby cutting bar 246 will sever the formed loop of suture wire from the suture wire remaining in the instrument, lift the trailing end of the suture loop and then push the suture loop free from the suturing instrument.

At the completion of the stroke, lever 104 is released, thereby allowing the aforementioned parts to return to their starting position under the influence of spring 116. However, one way clutches 312 and 320 (FIG. 19) interposed between drive rollers 306 and 314, and the drive rollers 306 and 314, respectively, prevent reverse movement of the drive rollers, thereby preventing any retraction of the suture wire.

Thus, a single throw of lever 104 will result in a predetermined degree of movement of drive rollers 306 and 314, which will in turn result in a predetermined length of suture wire being advanced out of the distal end of the suturing instrument.

It should be appreciated that each drive roller and axle assembly (i.e., drive roller 306 and axle 310, and drive roller 314 and axle 318) is preferably machined (i.e., turned) from a single, continuous piece of metal, using the same tool setup, so that the alignment of both is immune from the inaccuracies which might occur if they were turned at different occasions and assembled using holes and holding means. This construction is important, because the drive rollers are approximately 30 times the diameter of the suture wire they are driving and even the slightest alignment inaccuracies can rotate the wire as it is moved forward. Since the wire is permanently curved by the exit path in the end effector 204, any such wire rotation may cause the wire to swerve from its normal trajectory from the end effector and possibly prevent the leading tip of the wire from properly returning to the end effector after it has passed through the subject.

It should also be appreciated that peripheral grooves may be formed in drive rollers 306 and 314. Such grooves provide a seat for the suture wire being driven and help increase the surface area contact between the drive rollers and the suture wire.

Wire Supply Cartridge 400

Looking next at FIGS. 22-25, wire supply cartridge 400 generally comprises a spool housing 402, a wire spool 404, a spool retainer spring 406, a spool cover 408, a molded tube support 410 and a wire support tube 412. A length of suture wire 416 extends from spool 404 and through molded tube support 410 and wire support tube 412.

More particularly, a supply coil of suture wire 416 (comprising wire formed of metal or any other suitable material having the required flexibility and stiffness) may be supplied in the base of cartridge 400 and is fed into wire support tube 412. Wire support tube 412 surrounds suture wire 416 from spool housing 402 to the distal end of suturing instrument 2 where, with the distal end of wire support tube 412 received in channel 226 (FIG. 12), the suture wire enters second channel 228 in end effector 204. Wire support tube 412 ensures that suture wire 416 does not bend or buckle as the suture wire is pushed through handle assembly 100 and cannula assembly 200. More particularly, wire support tube 412 preferably forms a sufficiently close sliding fit with suture wire 416 such that suture wire 416 cannot bend or buckle as the suture wire is advanced through suturing instrument 2. At the same time, wire support tube 412 is also formed so as to present a minimum of friction to suture wire 416 as the suture wire is advanced through the instrument. The foregoing characteristics are important, inasmuch as suture wire 416 is extremely thin and flexible and highly susceptible to bending or buckling in the absence of some sort of lateral support.

By way of example but not limitation, where suture wire 416 is formed out of stainless steel and has a diameter of 0.017 inch, wire support tube 412 might have an inside diameter of 0.185 inch and an outside diameter of 0.050 inch. In addition, wire support tube 412 is preferably formed out of 316 stainless steel, however, it may alternatively be formed out of some other material. If desired, the interior of wire support tube 412 may be coated with a lubricant so as to facilitate closely-supported, low-friction passage of the suture wire through the wire support tube.

Wire support tube 412 and its surrounding molded tube support 410 have aligned openings 418 and 420, respectively, on opposite sides thereof. Openings 418 and 420 expose diametrically opposed portions of the suture wire 416 so that rollers 306 and 314 may contact suture wire 416 and urge the suture wire forward toward the distal end of suturing instrument 2, as will hereinafter be discussed in further detail.

As noted above, wire supply cartridge 400 may be loaded into wire drive assembly 300 by actuating lever 336 so as to force movable block 304 away from fixed block 302 and thereby separate rollers 306 and 314. Once roller 314 is separated from roller 306 by a sufficient distance, wire support tube 412 may be inserted between rollers 306 and 314, and then roller 314 returned towards roller 306 such that rollers 306 and 314 contact either side of suture wire 416 through the aligned openings 418 and 420 formed in either side of wire support tube 412 and its surrounding molded support tube 410, respectively.

Operation

Suturing instrument 2 may be used to apply loops 422 (FIG. 26) of wire suture 416 to a subject so as to effect a desired suturing operation.

By way of example but not limitation, and looking now at FIGS. 26-33, suturing instrument 2 may be used to suture together two portions 500, 502 of a subject which is to be sutured. In a typical case, portions 500, 502 might comprise two sections of severed tissue which need to be re-attached to one another, or two pieces of previously unattached tissue which need to be attached to one another. However, one or the other of the portions 500, 502 might also comprise artificial mesh or some other object which is to be attached to tissue, etc. In addition, in a typical case, portions 500, 502 might be located relatively deep within a patient, and might be accessed during an endoscopic or a so-called "minimally invasive" or a so-called "closed surgery", procedure; however, in other circumstances, portions 500, 502 might be accessed during a conventional, or so-called "open surgery", procedure. This latter situation might include procedures done at the outer surface of the patient's body, i.e., where portions 500, 502 comprise surface elements.

In any case, suturing instrument 2 is initially prepared for use by installing a wire supply cartridge 400 into the suturing instrument, if a cartridge 400 is not yet installed. As noted above, wire supply cartridge 400 is installed in suturing instrument 2 by (1) removing shroud 126, (2) moving the wire drive assembly's release lever 336 to its open position, so as to move rollers 306 and 314 apart; (3) passing the distal end of the cartridge (i.e., the distal end of wire support tube 412) through wire drive assembly 300 and cannula assembly 200 until the distal end of wire support tube 412 is located in the end effector's first channel 226, at which point the cartridge's molded tube support 410 will be positioned intermediate rollers 306 and 314; and (4) moving the wire drive assembly's release lever 336 back to its closed position, so that rollers 306 and 314 engage the suture wire 416 through openings 420 and 418, and so that spur gears 308 and 316 engage the teeth 118 of rack 114.

At this point suturing instrument 2 will be ready for use.

Figure 26:
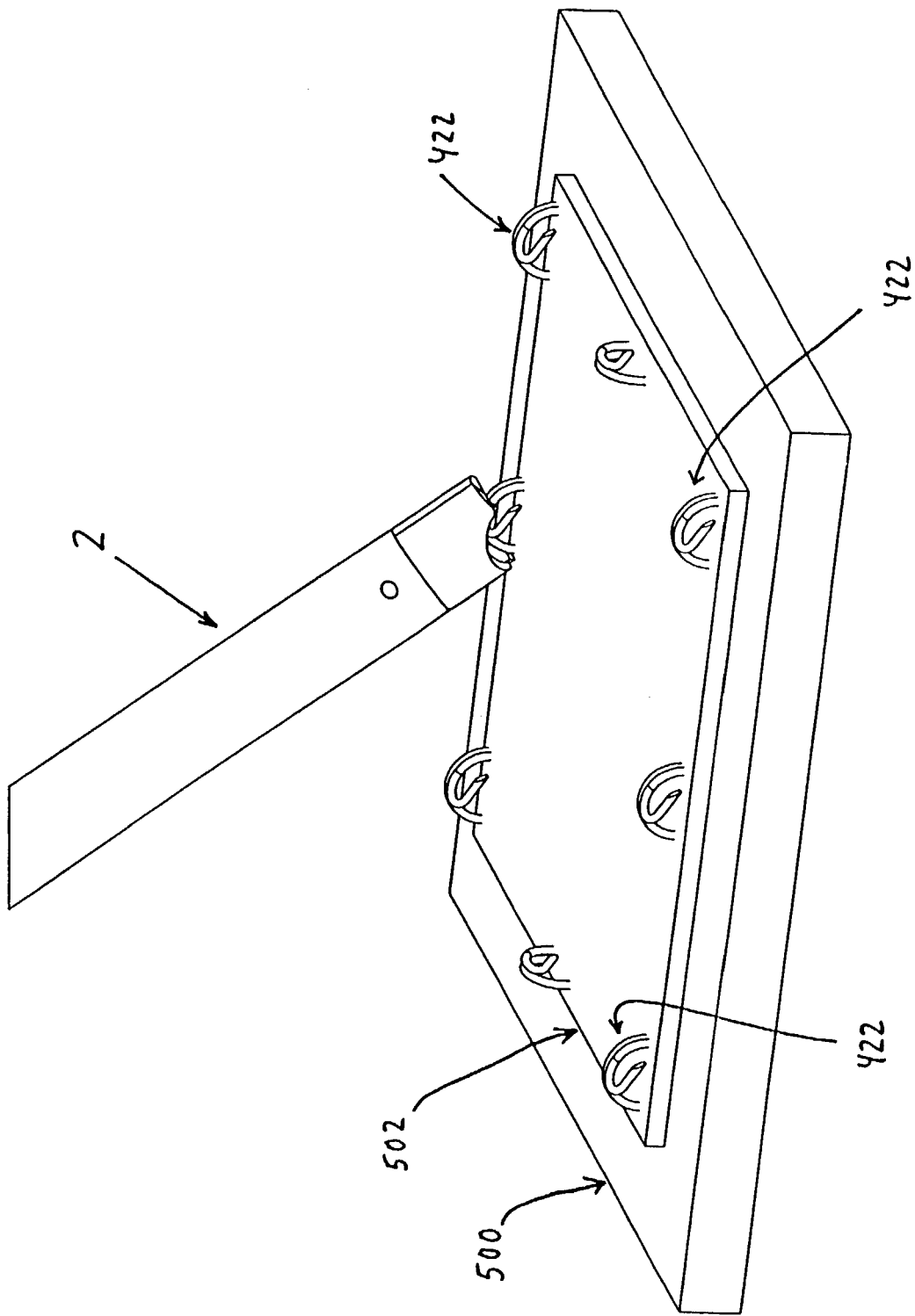
FIG. 26 is a schematic view showing two portions being secured to one another with a suture loop deployed by the suturing instrument.
Figure 27:
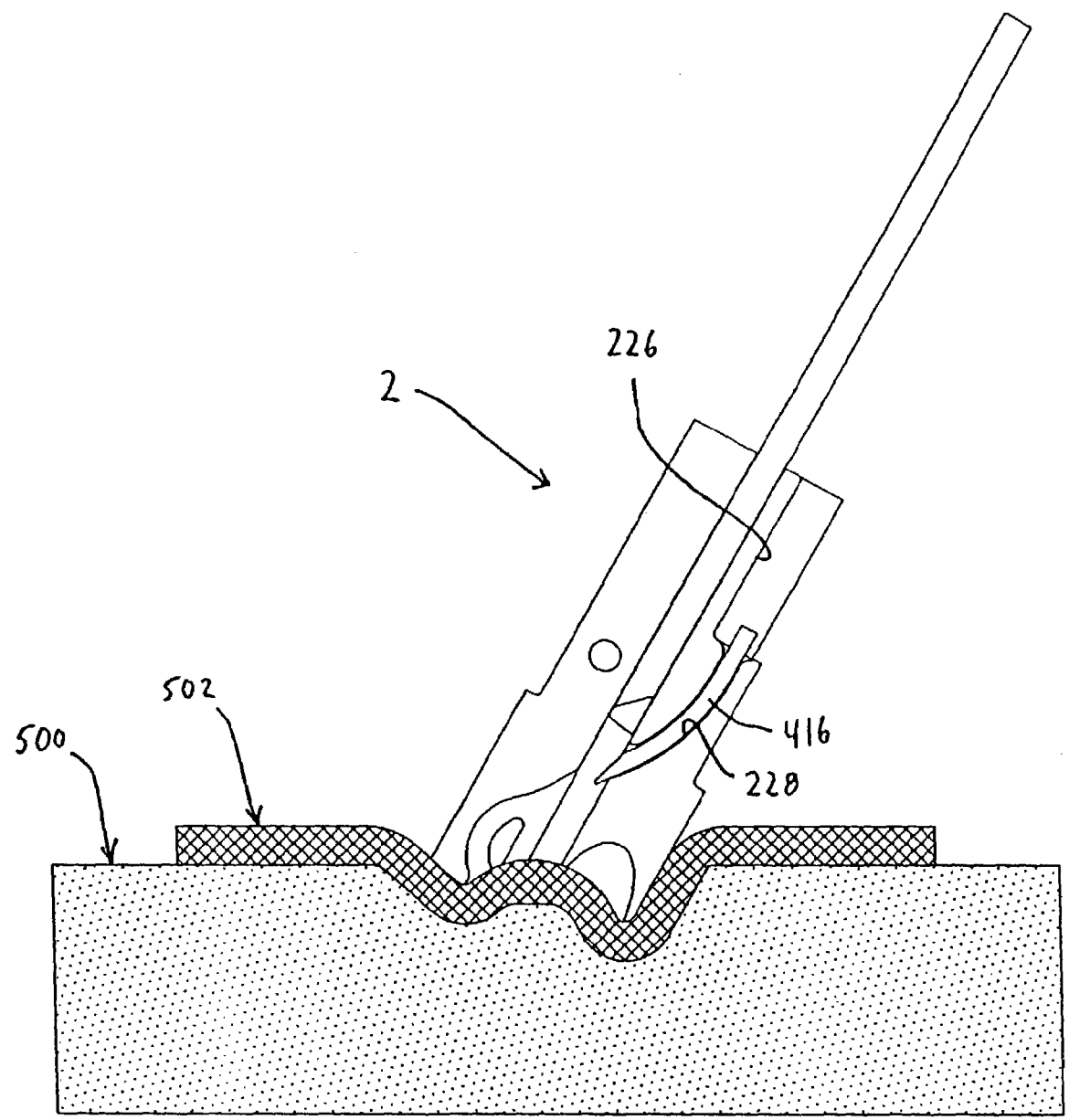
FIGS. 27-33 show various steps in a suturing operation conducted with the suturing instrument.
Figure 28:
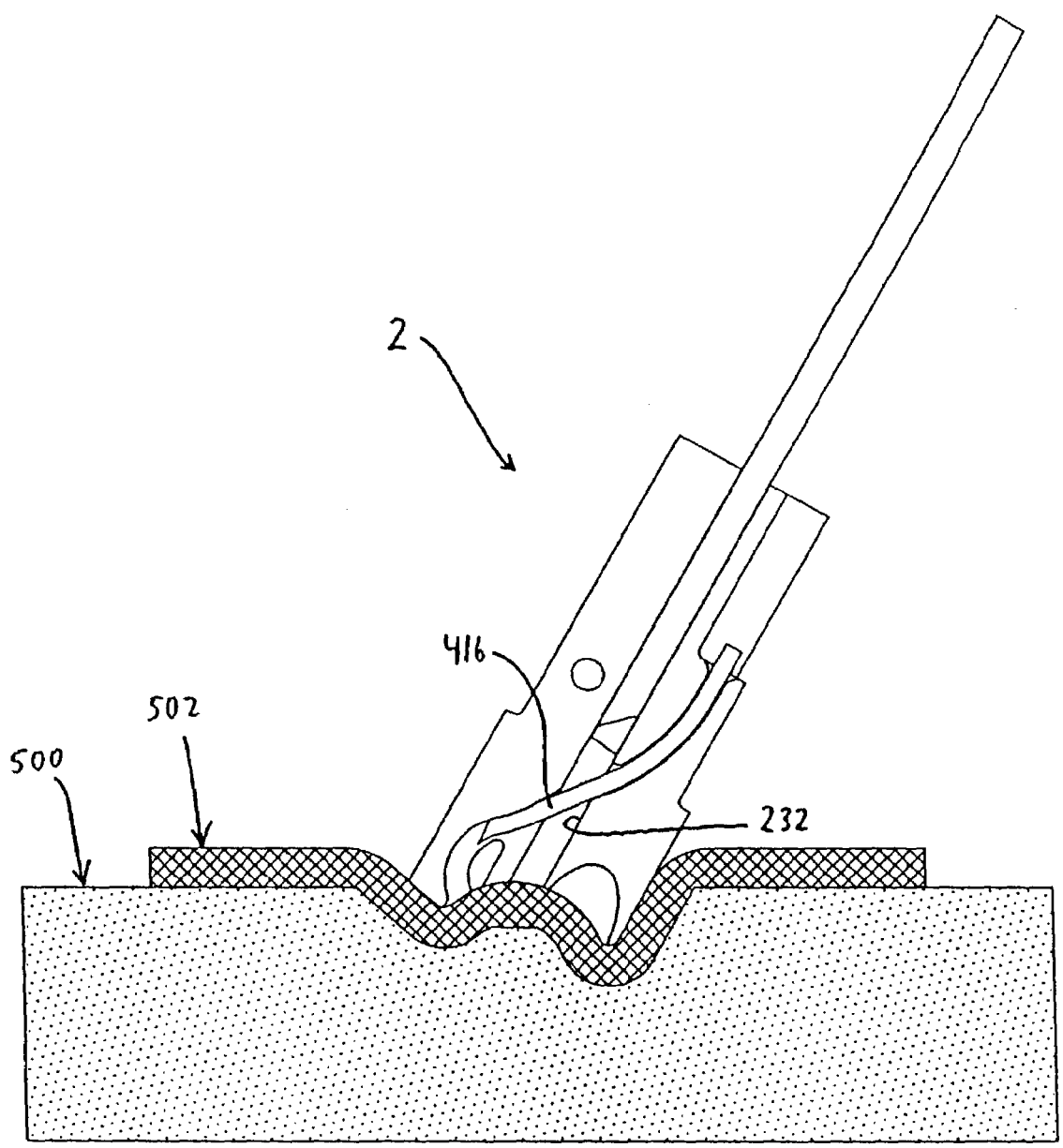

When suturing instrument 2 is to apply a suture loop 422 to a subject, the distal end of the suturing instrument is positioned against the subject, e.g., it is positioned against portions 500, 502 (FIGS. 26 and 27).

Figure 29:
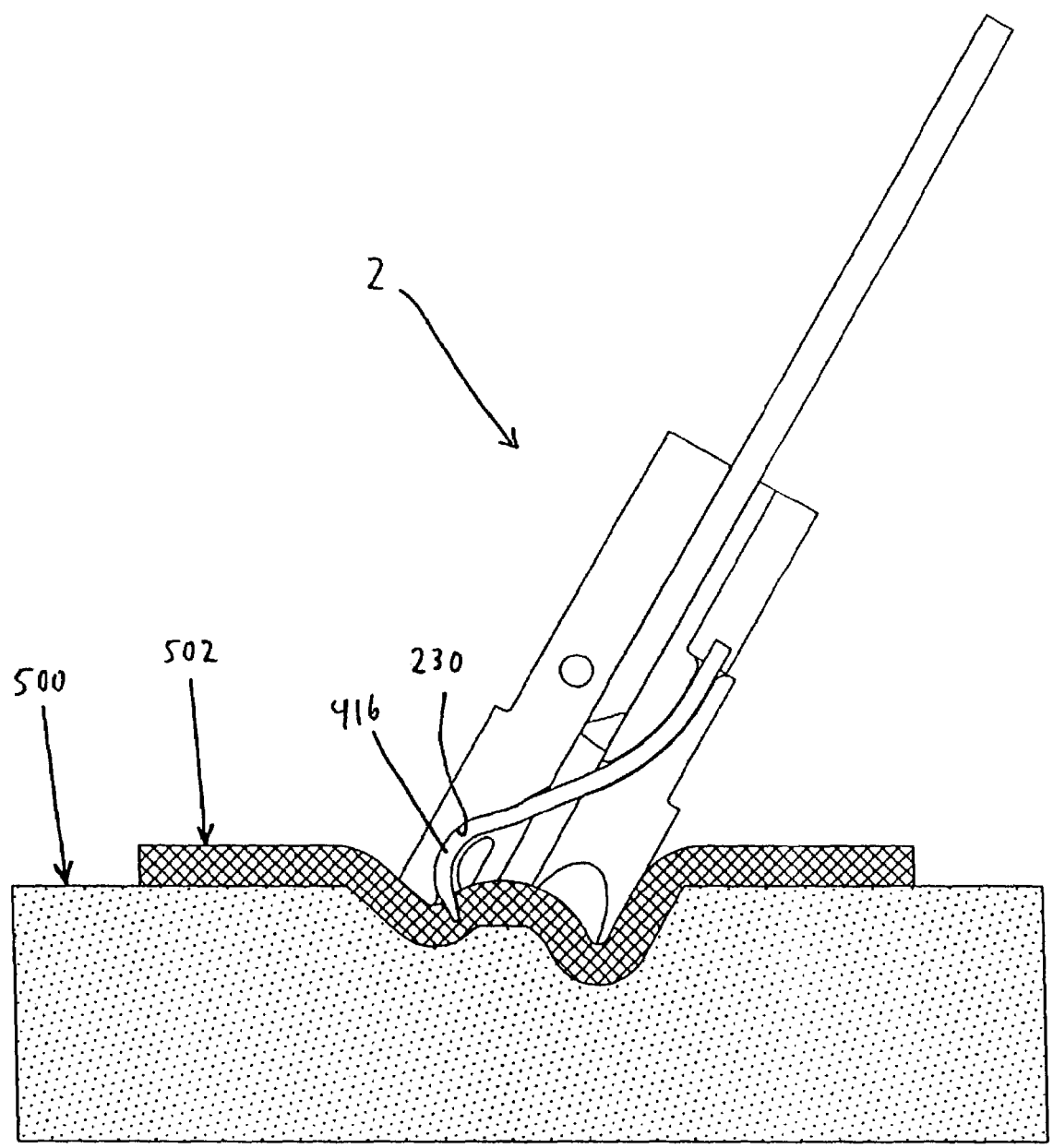
Figure 30:
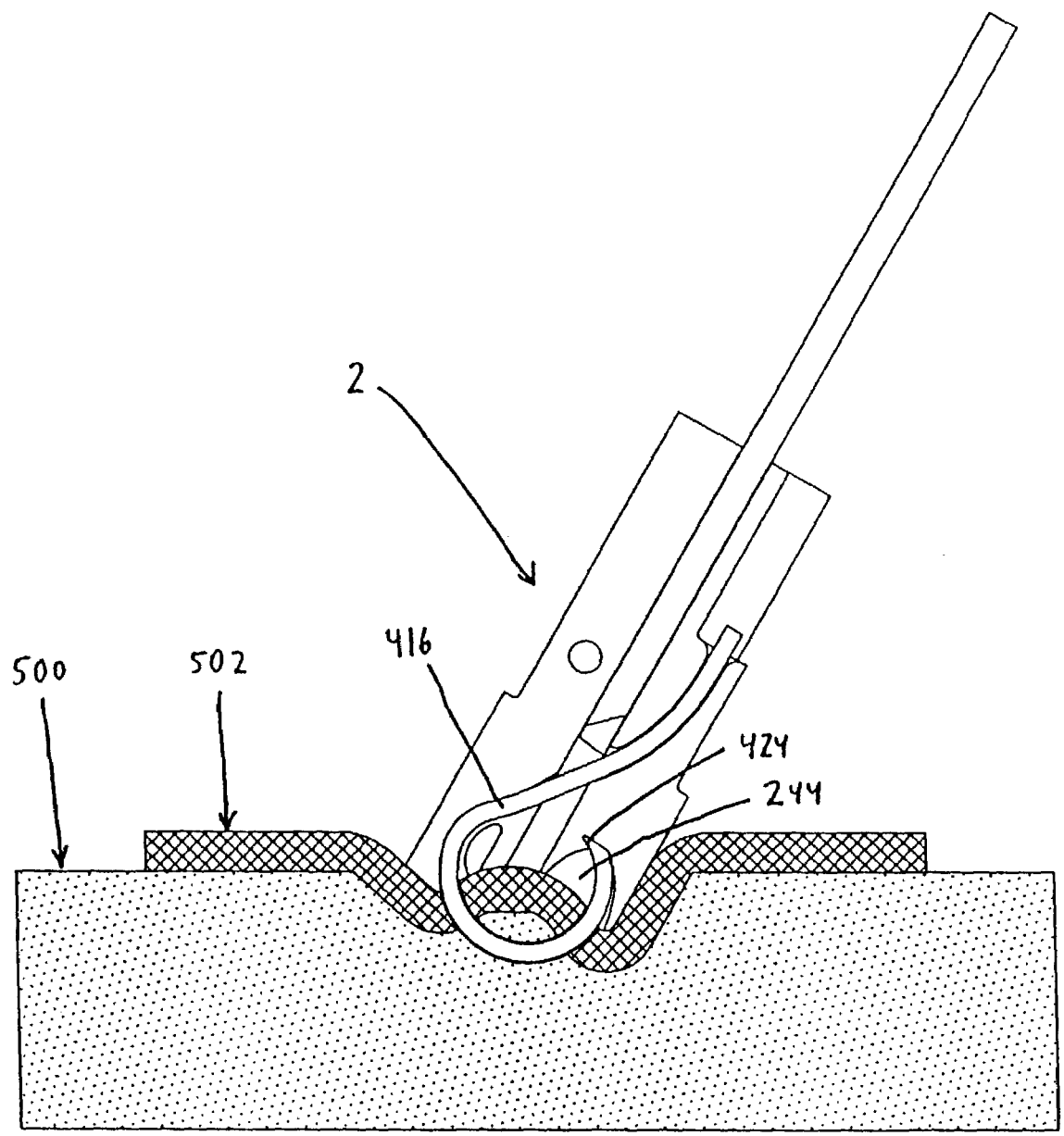
Figure 31:
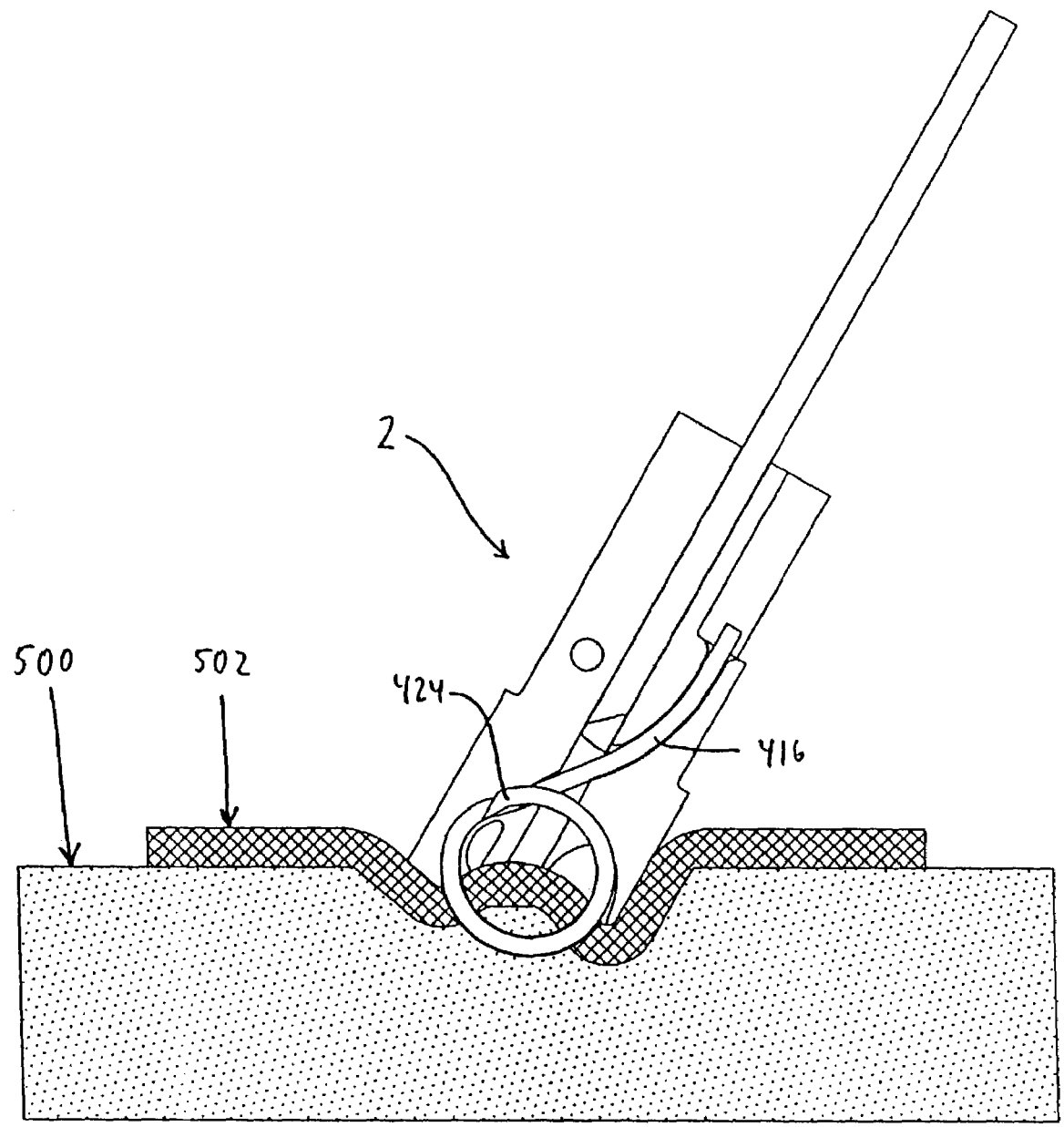

Once the distal end of suturing instrument 2 has been placed against subject portions 500, 502, lever 104 is pulled back against handle 102. As the top end of lever 104 moves distally, rack 114 is also moved distally, whereby rack teeth 118 will cause spur gears 308 and 316, and hence rollers 306 and 314, to rotate. Rotation of rollers 306 and 314 in turn causes suture wire 416 to advance out of the distal end of wire support tube 412 (FIG. 27). The suture wire advances down second channel 228, across cutter bar channel 232 (FIG. 28), through second channel 230 and then out of the instrument (FIG. 29). Due to the curved geometry of channel 230, the suture wire emerging from end effector 204 will take on a set, causing it to curl in a loop fashion, whereby the suture wire will pass through the material to be sutured and then back into slot 264 in the end effector's fixed second portion 224 (FIG. 30). To assist the returning wire into slot 264, the guide surface 244 may be provided at the distal end of end effector 204.

If desired, the proximal end 276 (FIG. 17) of slot 264 in the end effector's fixed second portion 224 can act as a sort of deflecting anvil to receive and redirect the suture wire 416 received from third channel 230. In such a case, slot 264 actually helps form loop 422. However, in accordance with the present invention, it is not necessary for slot 264 to act as a deflecting anvil for suture wire 416, since the curvature of loop 422 can be imparted solely by the geometry of third channel 230 if desired.

Figure 32:
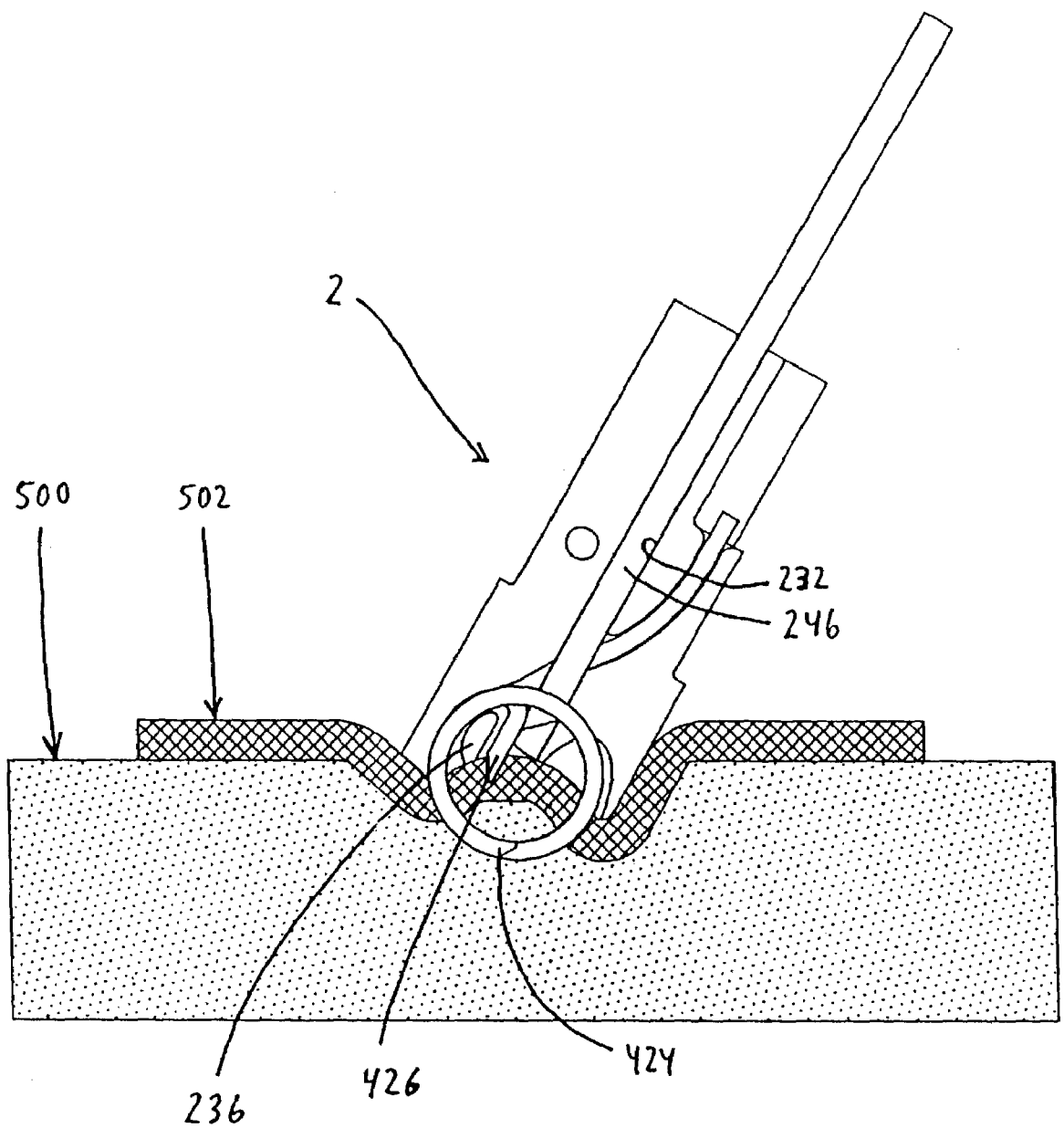

Suture wire 416 is advanced a predetermined amount, i.e., the correct amount to form the desired loop construct. In other words, where a "Q-form loop" 422 is to be formed, suture wire 416 is advanced so that the leading end 424 (FIG. 30) of the suture wire passes across cutting bar passageway 232 (FIG. 31) and back out of the instrument until the leading end 424 of the suture wire is intermediate the front end of the tool (FIG. 32). At this point the advancement of suture wire 416 is stopped.

As noted above, in the preferred embodiment of the invention, the length of suture wire advanced out of the distal end of the instrument is regulated by the length of the teeth 118 placed on rack 114. More particularly, the initial movement of lever 104 toward handle 102 causes the toothed portion 118 of rack 114 to move past spur gears 308 and 316, whereby to rotate drive rollers 306 and 314 and hence advance suture wire 416. Further movement of lever 104 toward handle 102 causes the smooth wall 120 of rack 114 to move past spur gears 308 and 316, which results in no movement of spur gears 308 and 316 and hence no advancement of suture wire 416. Thus, the length of toothed portion 118 of rack 114 regulates the extent of suture wire drive.

However, in accordance with the present invention, continued movement of lever 104 toward handle 102 causes the distal end of the lever to engage the proximal end 260 of the cutting bar 246, whereby to drive the cutting bar distally (FIG. 32). This causes the cutting bar 246 to (i) first encounter, and then sever, the proximalmost portion 426 of the suture wire extending across cutting bar passageway 232, whereby to separate loop 422 from the remainder of the suture wire carried by the suturing tool, and (ii) then drive against the end 426 of loop 422 whereby, with the assistance of island 236, to bend the end 426 toward the material being joined.

Significantly, at the same time that this bending is occurring, inasmuch as cutting bar 246 includes ejection ramp face 254 and ejection push face 258 at the distal end thereof, and inasmuch as the end effector's fixed second portion 224 includes the slot 264 to form a gap in the end of the end effector, distal movement of cutting bar 246 will also serve to lift loop 422 up over island 236 and push it free from the suturing instrument, whereby to disengage the formed loop 422 from the distal end of suturing instrument 2. Furthermore, if desired, cutting bar channel 232 may be offset from the plane of wire channels 228 and 232 so as to further assist lifting loop 422 up over island 236. In addition, if desired, island 236 may be formed so as to be mechanically retractable into the body of fixed first portion 222, whereby to further facilitate disengagement of the formed loop 422 from the suturing instrument.

Figure 33:
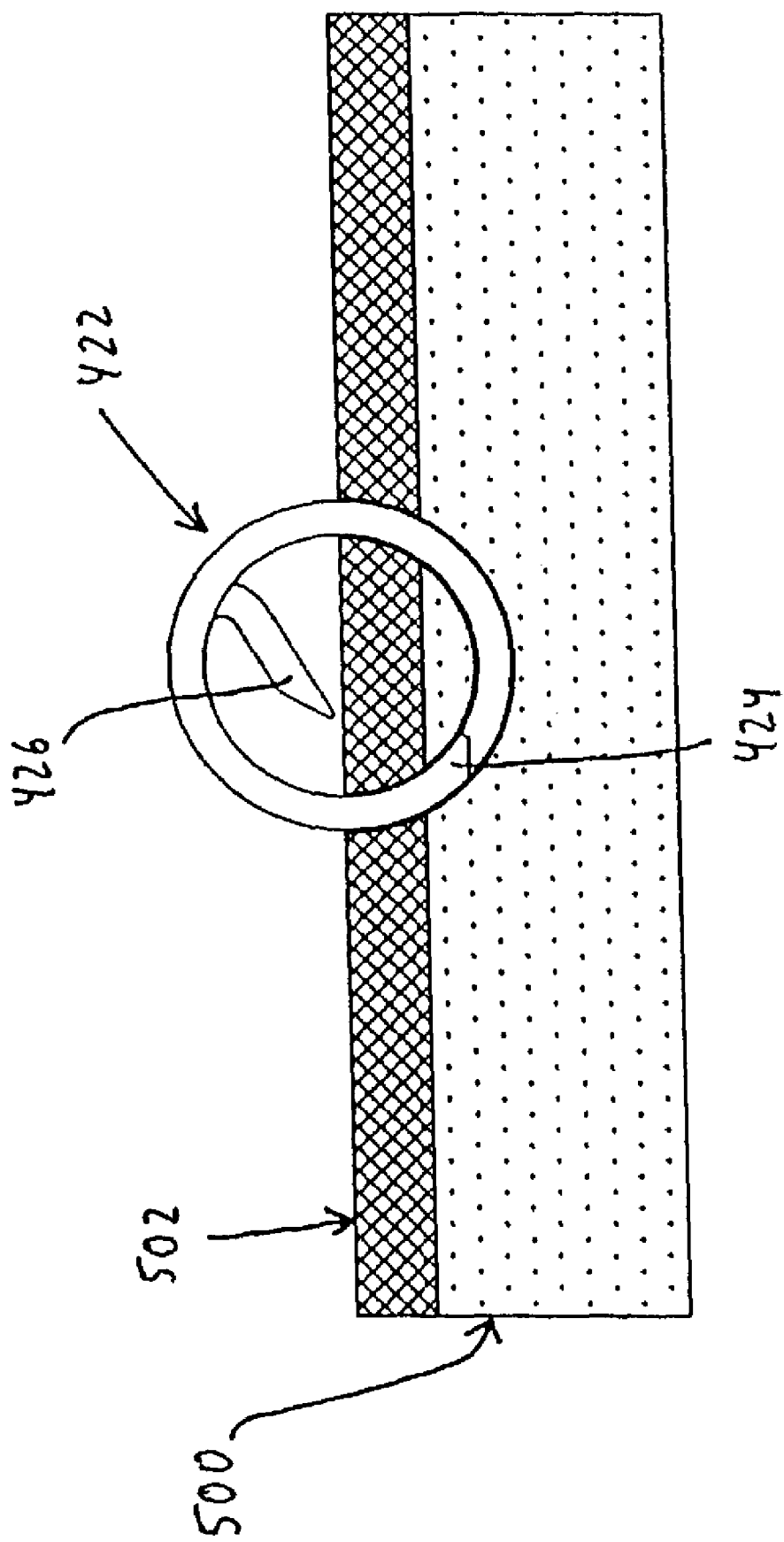

Due to the manner in which loop 422 is formed, the trailing end 426 of the loop will project distally, into the material being formed (FIG. 33). This feature is generally highly desirable, since it produces a secure, low profile fixation.

Various factors can affect how the wire element loops in the tissue. These factors include instrument-related factors (e.g., the curvature of third channel 230, etc.), wire-related factors (e.g., wire tensile strength, wire yield stress, wire diameter, etc.) and tissue-related factors (e.g., tissue density, tissue elasticity, tissue thickness, tissue stabilization, etc.).

The aforementioned factors are preferably taken into account when forming wire loops in tissue. For example, when forming a loop in intestine, which tends to be a relatively delicate tissue, it is generally preferable to use a relatively "soft" wire; correspondingly, when forming a loop in the abdominal wall, which tends to be a relatively tough tissue, it is generally preferable to use a relatively "hard" wire.

In general, it has been found that suture wire formed out of 316 LVM stainless steel, having a tensile strength of 230-260 kpsi and a diameter of about 0.006-0.019 inch, is advantageous in particular applications. In general, when forming suture loops with a diameter of about 0.140-0.165 inch, it has been found acceptable to provide third channel 230 with a radius of 0.050-0.075 inch.

It should be appreciated that the suture loop 422 can, if desired, have a diameter which exceeds the diameter of suturing instrument.

It should also be appreciated that, due to the fact that cannula assembly 200 can be dismounted from handle assembly 100, a set of different cannula assemblies, each having different loop-forming characteristics, can be provided to the user for appropriate selection at the time of use.

In a similar fashion, due to the fact that wire supply cartridge 400 can be dismounted from suturing instrument 2, a set of different wire supply cartridges, each having different suture wire characteristics (e.g., material, hardness, diameter, etc.) can be provided to the user for appropriate selection at the time of use.

If desired, loop 422 can be used to secure mesh 502 to tissue 500, or to attach other objects to tissue, or to attach objects other than tissue together, etc. In this respect it should be appreciated that where the suturing instrument is to be used to secure mesh to tissue, and where end effector 204 is provided with stabilizing projections 272, 274 (FIGS. 12 and 17), projections 272, 274 are preferably formed narrow enough and long enough to extend completely through the mesh and contact the underlying tissue.

Figure 34:
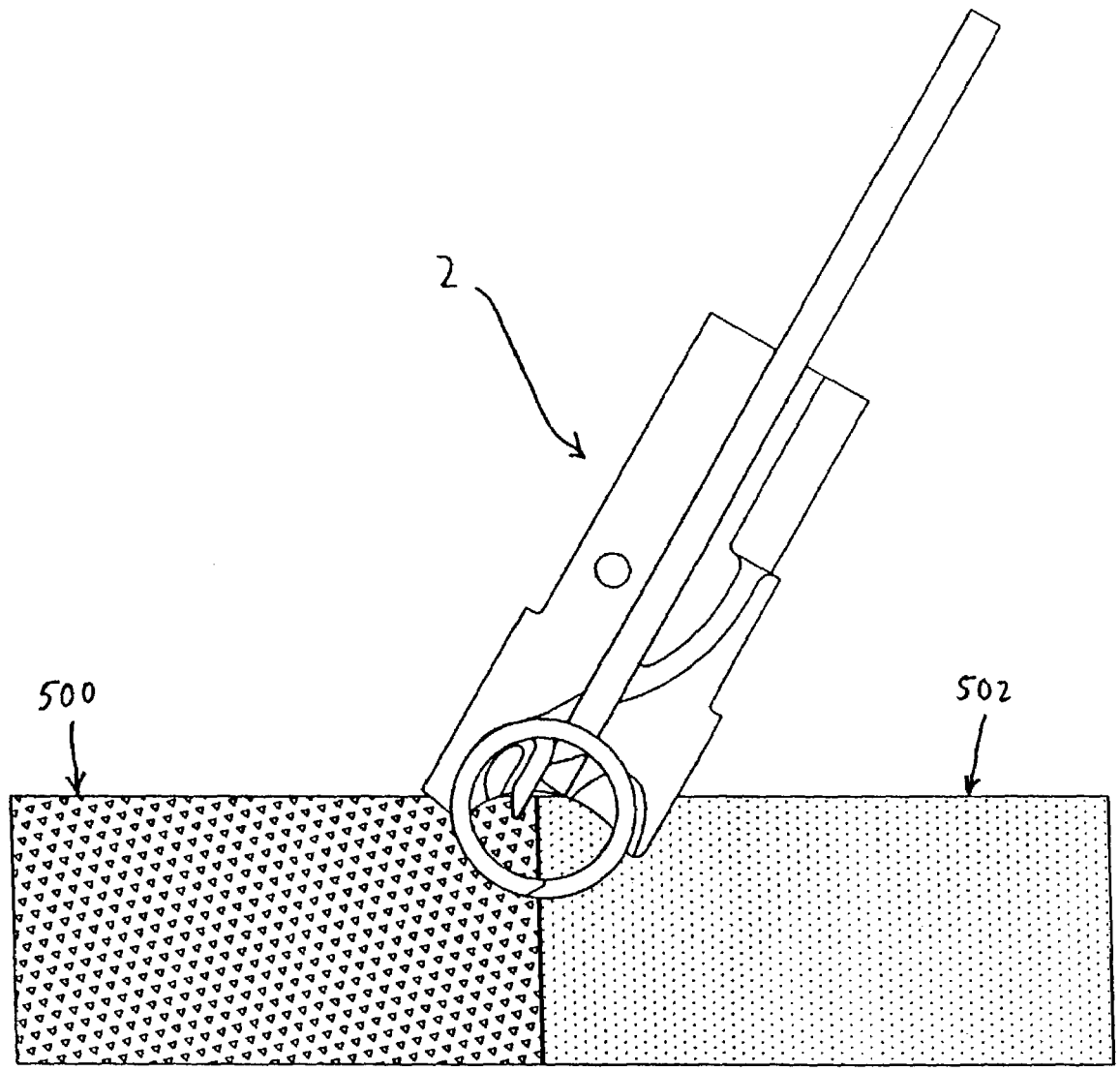
FIG. 34 is a schematic view showing an alternative form of tissue attachment being effected with the suturing instrument.

In addition to the foregoing, in FIGS. 26-33, suturing instrument 2 is shown securing one layer of material 502 to an underlying layer of material 500. However, it should also be appreciated that other types of attachments may also be formed with suture loop 422. Thus, for example, in FIG. 34 two portions 500, 502 are shown being secured to one another in a so-called "end to end" configuration.

Figure 35:
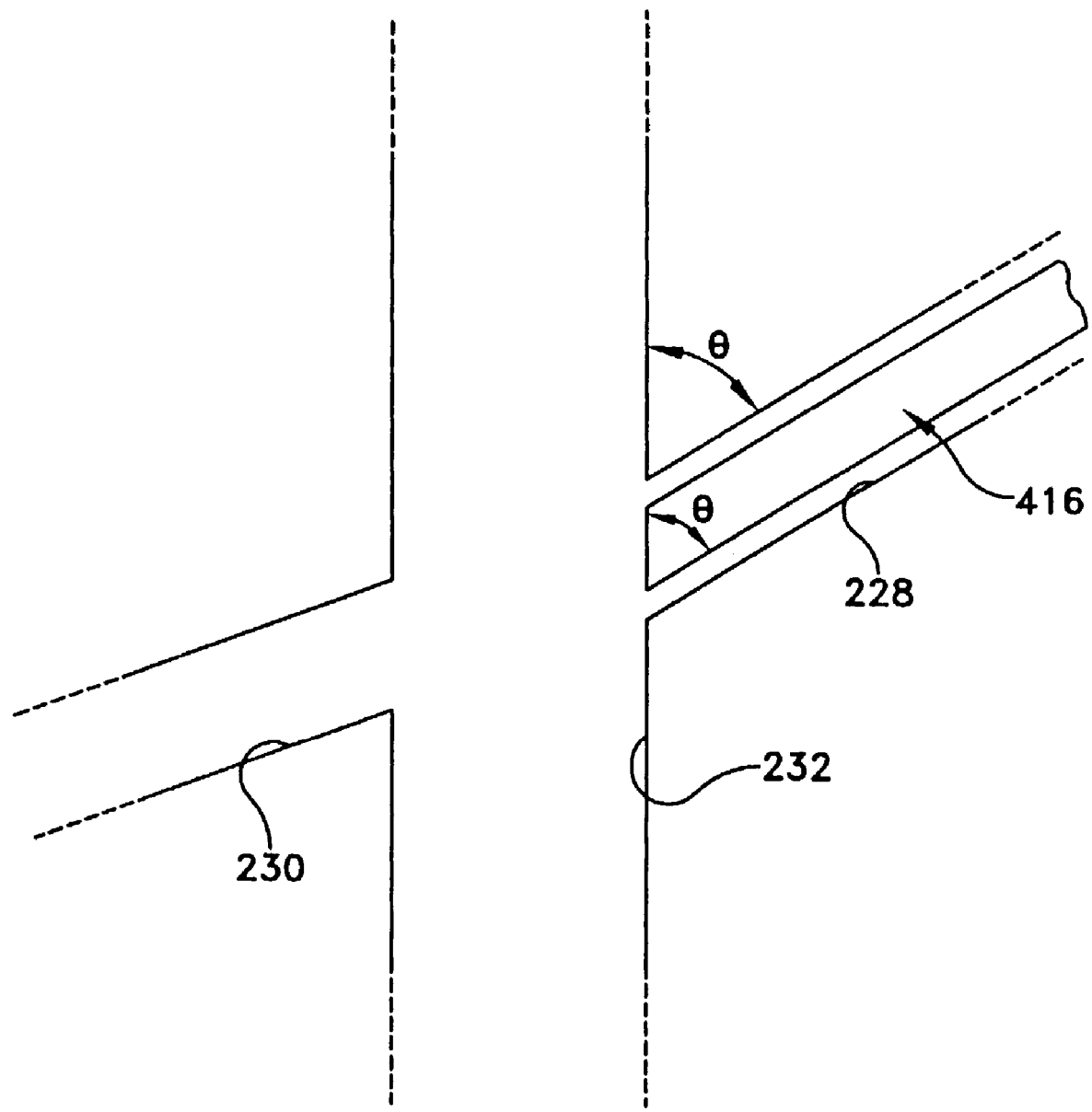
FIGS. 35-37 are schematic side views illustrating the inter-relationship between the geometry of the cannula assembly's end effector portion and the leading tip of the suture wire.

As noted above, channels 228 and 230 are positioned on opposing sides of cutting bar channel 232, whereby a length of suture wire 416, extending between channels 228 and 230, may be severed by cutting bar 246. In this respect it will be appreciated that the angle at which cutting bar channel 232 intersects channel 228 has a bearing on the angle imparted to the leading tip 424 of suture wire 416. More particularly, in FIG. 35 it will be seen that cutting bar channel 232 intersects second channel 228 at the angle θ; as a result, the leading tip of suture wire 416 will also be set at the angle θ.

Figure 36:
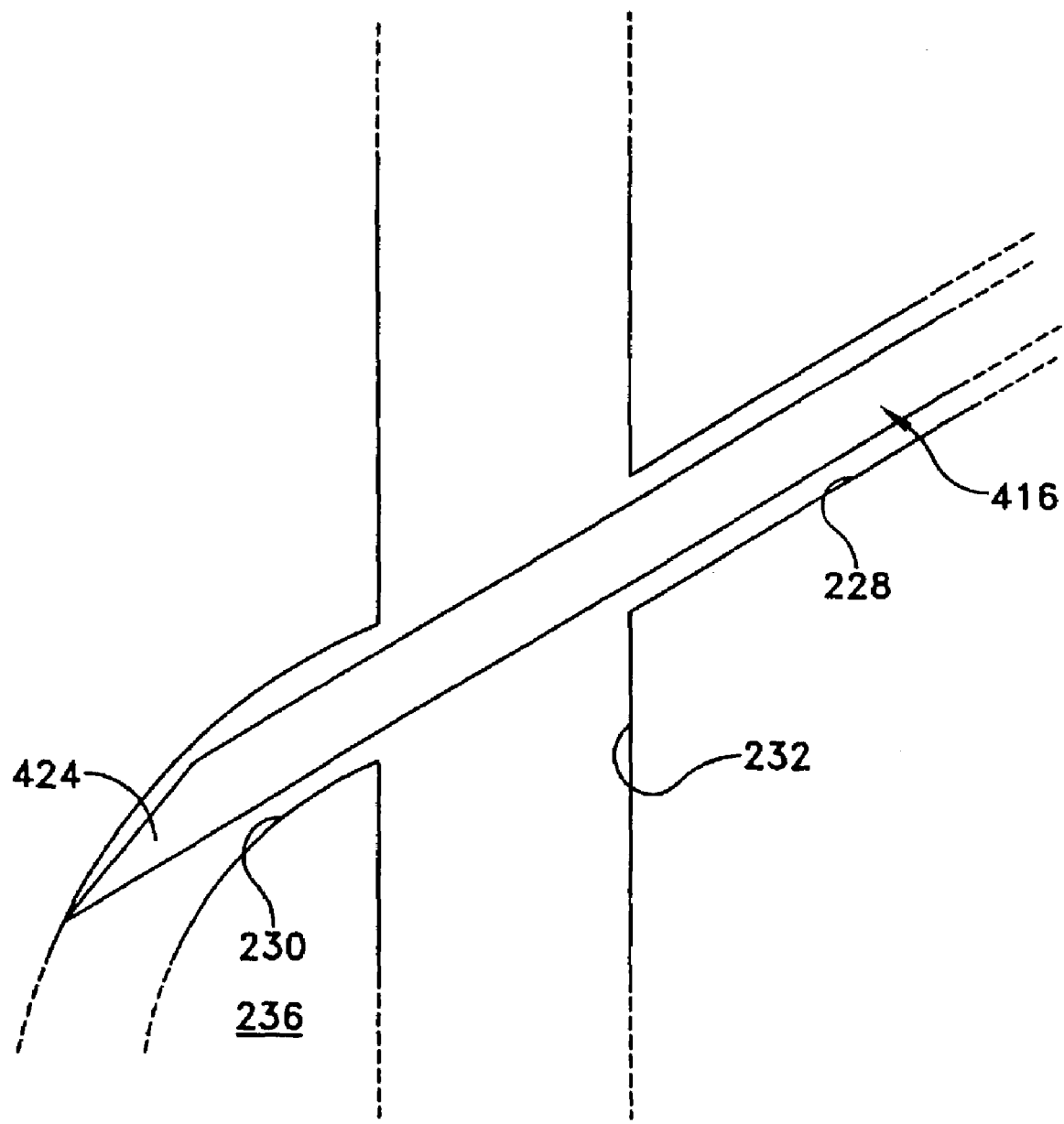
Figure 37:
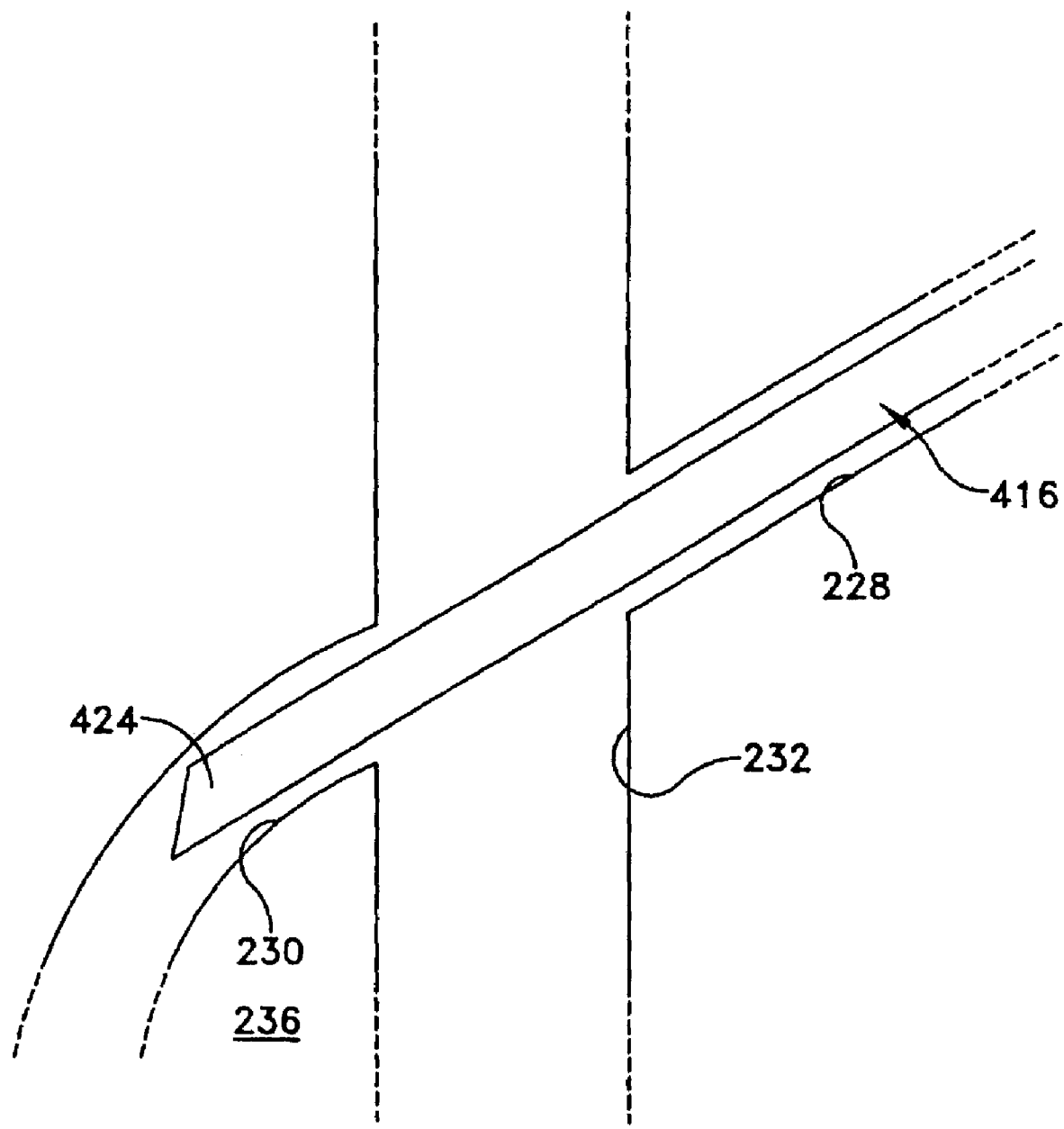

In general, when considered solely from the standpoint of tissue penetration, it is typically desirable that the angle θ be as small as possible, in order that the suture wire have the sharpest possible tip to facilitate tissue penetration. At the same time, however, it must also be appreciated that the leading tip of suture wire 416 must traverse the substantial curvature of third channel 230 and, if the angle θ is too small, the sharp leading tip of the suture wire will strike the wall of third channel 230 (FIG. 36) and thereby become damaged and/or blunted. On the other hand, if the angle θ is increased, the heel of the tip will engage the wall of third channel 230 (FIG. 37), thereby leaving the sharp tip of the suture wire undamaged. Thus, it is generally preferred that the angle θ be set so that the leading tip of suture wire 416 be formed as sharp as possible while still being able to traverse the curvature of third channel 230 without damage.

Figure 38:
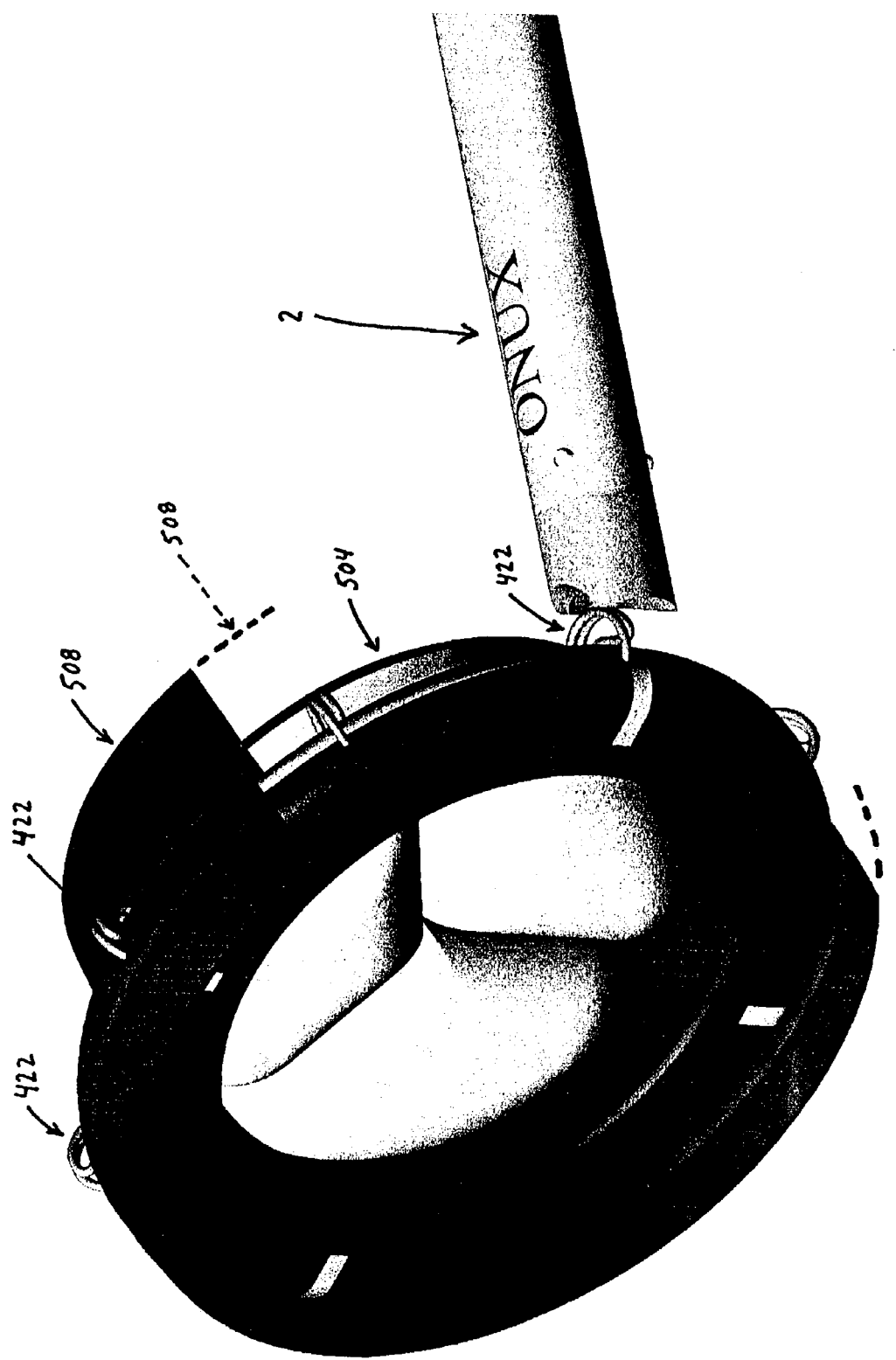
FIG. 38 is a schematic view showing the suturing instrument securing a prosthetic cardiac valve to vascular tissue with suture loops.

As noted above, suture loop 422 can be used to secure tissue to tissue, or to secure an inanimate object to tissue, or to secure an inanimate object to an inanimate object, etc. In this respect it should be appreciated that one anticipated application for suture loop 422 is to secure a prosthetic cardiac valve to a valve seat within the heart. See, for example, FIG. 38, where suturing instrument 2 is shown securing a prosthetic cardiac valve 504 to vascular tissue 508 (in this respect it should be appreciated that in FIG. 38, a portion of the vascular tissue 508 has been removed so as to illustrate how suture loops 422 penetrate a portion of cardiac valve 504).

In the foregoing description, suture wire 416 is described as comprising an elongated length which is cut into specific lengths at the time of use by the action of cutting bar 246. In this respect it should also be appreciated, however, that suture wire 416 may be pre-cut into selected lengths prior to use, and the pre-cut lengths then stored in a magazine or the like, for deployment at the time of use. In such a case, cutting bar 246 will act as a forming and ejecting tool rather than as a cutting, forming and ejecting tool.

As noted above, suture wire 416 may comprise a wire formed out of a metal or any other suitable material having the required flexibility and stiffness. By way of example but not limitation, suture wire 416 may comprise stainless steel, titanium, tantalum, etc.

If desired, suture wire 416 may also be coated with various active agents. For example, suture wire 416 may be coated with an anti-inflammatory agent, or an anti-coagulant agent, or an antibiotic, or a radioactive agent, etc.

MODIFICATIONS

It will be appreciated by those skilled in the art that numerous modifications and variations may be made to the above-disclosed embodiments without departing from the spirit and scope of the present invention.

Thus, for example, shaft 202 has been shown as being substantially straight; however, it is also anticipated that shaft 202 may be curved along its length. Furthermore, shaft 202 may be substantially rigid, or it may be flexible so that it can be bent along its length. It is also possible to form shaft 202 so that it has two or more articulating sections so as to aid in the positioning of end effector 204.

What is claimed is:

1. A suturing instrument comprising:
a handle;
a shaft extending from the handle and having a proximal end and a jawless distal end, an opening near the distal end, and an island near the opening;
a first channel adapted to guide a suture wire in movement toward the distal end;
a second curved channel configured to receive suture wire from the first channel and shaped to impart a curvature to the suture wire as the suture wire moves in the second curved channel, the second curved channel communicating with the opening; and
a wire drive adapted to move the suture wire in the second curved channel and away from the distal end upon exiting the opening to form a loop of suture wire, the instrument including a cutting bar that moves to bend a trailing end of the suture wire around the island so that a portion of the trailing end extends inwardly of the loop.

2. The instrument of claim 1, wherein the second curved channel and the opening are arranged so that the suture wire extends in a generally distal direction upon exiting the opening.

3. The instrument of claim 1, wherein when the wire drive moves the suture wire in the second curved channel, a free end of the suture wire moves from the opening and follows a curved path so that the free end moves back toward the instrument.

4. The instrument of claim 1, wherein the wire drive is adapted to move the suture wire from the opening with force sufficient so that a free end of the suture wire can puncture tissue.

5. The instrument of claim 1, wherein the loop of suture wire is an approximately circular loop of suture wire formed as suture wire is driven out of the opening in the distal end.

6. The instrument of claim 5, wherein the circular loop is formed at an extreme axial end of the shaft.

7. The instrument of claim 1, further comprising:
a cutter adapted to cut the suture wire so as to form a sharp point on the suture wire.

8. The instrument of claim 1, further comprising:
a cutter adapted to cooperate with a portion of the second curved channel to cut the suture wire.

9. The instrument of claim 1, further comprising:
a cutter that includes a cutting bar adapted to move axially to cut the suture wire.

10. The instrument of claim 1, further comprising:
a cutter adapted to cut the suture wire so that a formed loop of suture wire is freed from suture wire remaining attached to the instrument.

11. The instrument of claim 10, wherein the cutter includes an ejection ramp face adapted to lift a portion of the formed loop of suture wire out of the second curved channel.

12. The instrument of claim 10, wherein the cutter includes an ejection push face adapted to direct the formed loop of suture wire away from the distal end.

13. The instrument of claim 1, wherein the wire drive is adapted to move the suture wire in an axial direction within the shaft.

14. The instrument of claim 1, wherein the second curved channel includes an "S" shaped passageway portion with a convex portion and a concave portion.

15. The instrument of claim 14, further comprising:
a cutter adapted to cut the suture wire at a location near where the convex portion and the concave portion meet.

16. The instrument of claim 1, further comprising:
a continuous length of suture wire, and wherein the instrument is adapted to form a plurality of loops of suture wire from the continuous length of suture wire.

17. The instrument of claim 1, wherein the instrument is adapted for use in a minimally invasive surgical procedure.

18. The instrument of claim 1, wherein the distal end of the shaft includes an angled end face.

19. The instrument of claim 18, wherein the instrument is arranged to form the loop of suture wire loop in tissue by positioning the angled end face adjacent the tissue and driving the suture wire through the second curved channel such that a free end of the suture wire punctures the tissue and follows a loop-like trajectory.

20. The instrument of claim 1, further comprising:
a slot at a distal face of the distal end, the slot adapted to receive a portion of suture wire that forms the loop.

21. The instrument of claim 20, wherein the slot includes a curved surface adapted to closely fit a loop of suture wire received in the slot.

22. The instrument of claim 20, wherein the slot includes a scalloped surface adapted to guide a free end of suture wire into the slot.

23. The instrument of claim 1, wherein the loop of suture wire has a spiral shape with a leading end that is adjacent to a trailing portion of the suture wire.

24. The instrument of claim 1, further comprising:
a cutter adapted to both cut the trailing end of suture wire forming the loop and bend a portion of the trailing end inwardly toward the center of the loop.

25. The instrument of claim 1, further comprising:
a removable cartridge including a length of suture wire that is provided to the wire drive.

26. The instrument of claim 25, wherein the removable cartridge includes a wire guide adapted to be received in the first channel.

* * * * *